United States Patent
Sikora et al.

(10) Patent No.: US 12,383,307 B2
(45) Date of Patent: Aug. 12, 2025

(54) SUTURE SYSTEM AND METHOD

(71) Applicant: Arthrosurface Incorporated, West Bridgewater, MA (US)

(72) Inventors: George Sikora, Bridgewater, MA (US); Steven W. Ek, Durham, NH (US)

(73) Assignee: ARTHROSURFACE INCORPORATED, West Bridgewater, MA (US)

( * ) Notice: Subject to any disclaimer, the term of this patent is extended or adjusted under 35 U.S.C. 154(b) by 0 days.

(21) Appl. No.: 18/132,711

(22) Filed: Apr. 10, 2023

(65) Prior Publication Data

US 2023/0355277 A1    Nov. 9, 2023

Related U.S. Application Data

(63) Continuation of application No. 16/917,207, filed on Jun. 30, 2020, now Pat. No. 11,648,036, which is a continuation of application No. 15/351,530, filed on Nov. 15, 2016, now Pat. No. 10,695,096, which is a continuation of application No. 13/863,917, filed on Apr. 16, 2013, now Pat. No. 9,492,200.

(51) Int. Cl.
| | |
|---|---|
| A61B 17/68 | (2006.01) |
| A61B 17/04 | (2006.01) |
| A61B 17/16 | (2006.01) |
| A61B 17/56 | (2006.01) |
| A61B 17/84 | (2006.01) |

(52) U.S. Cl.
CPC ........ *A61B 17/683* (2013.01); *A61B 17/0401* (2013.01); *A61B 17/1682* (2013.01); *A61B 2017/565* (2013.01); *A61B 17/842* (2013.01)

(58) Field of Classification Search
CPC ............ A61B 17/0401; A61B 17/1682; A61B 17/683; A61B 17/842; A61B 2017/564; A61B 2017/565
See application file for complete search history.

(56) References Cited

U.S. PATENT DOCUMENTS 10,695,096 B2 * 6/2020 Sikora .................. A61B 17/683
2010/0125297 A1 * 5/2010 Guederian ......... A61B 17/0401
                                                            606/232

* cited by examiner

*Primary Examiner* — Robert A Lynch
(74) *Attorney, Agent, or Firm* — Grossman, Tucker, Perreault & Pfleger, PLLC

(57) ABSTRACT

A suture system including a suture construct having a first reduction construct configured to be selectively arranged in an expanded state and a reduced state. The first reduction construct includes a first locking limb, a first contractible loop, and a first opposed loop disposed generally opposite to the first contractible loop, wherein reduction of the first opposed loop contracts the first contractible loop from the expanded state into the reduced state and secures the suture construct in the reduced state. The suture construct may also include a second reduction construct. Optionally, the suture system includes a first and a second pusher tube defining a first and a second lumen, respectively, wherein each pusher tubes are advanced over portions of opposed loops, respectively, and wherein distal portions of opposed loops extend beyond the pusher tubes, respectively.

14 Claims, 21 Drawing Sheets

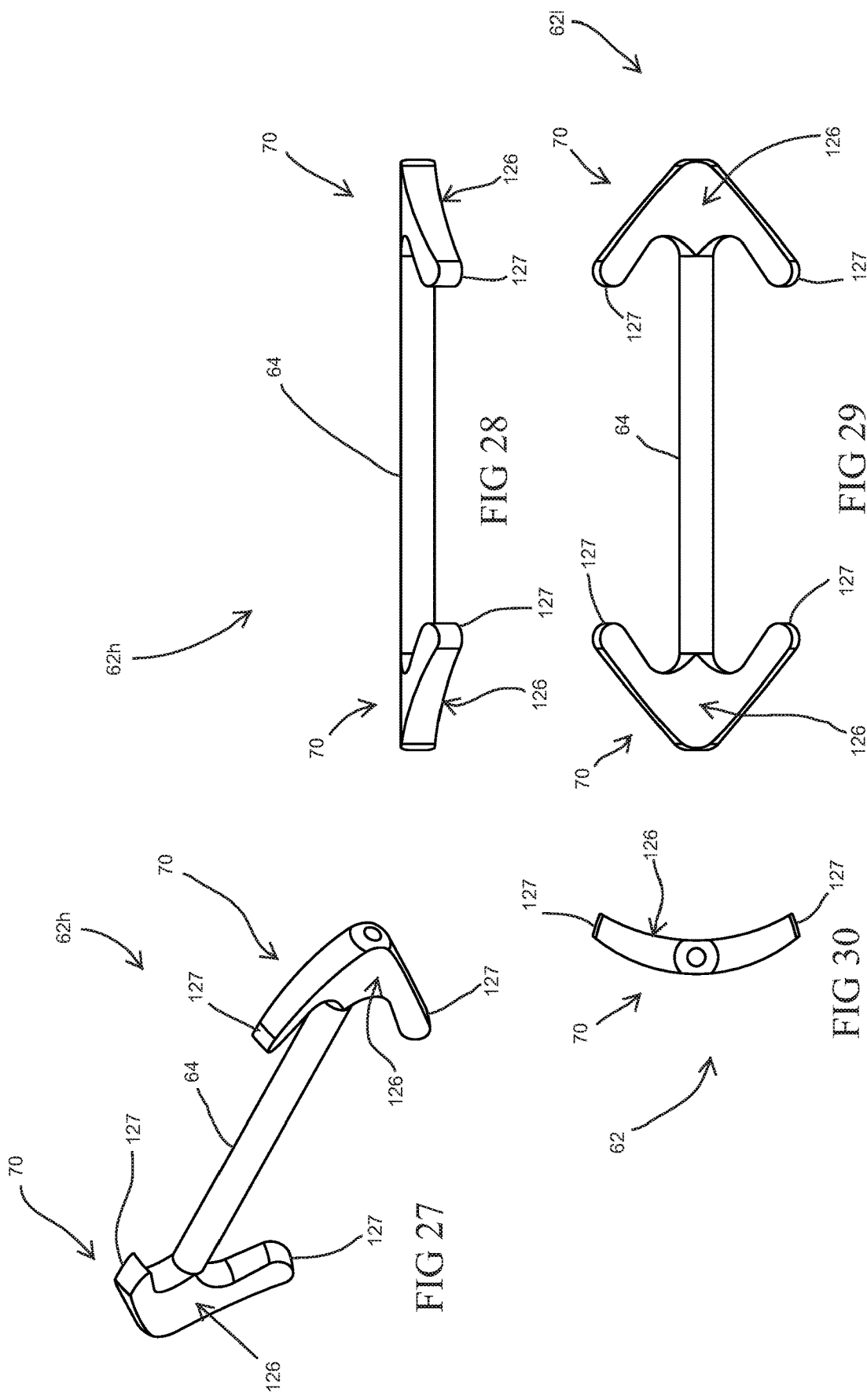

SUTURE SYSTEM AND METHOD

CROSS-REFERENCE TO RELATED APPLICATIONS

This application is a continuation of U.S. patent application Ser. No. 16/917,207, filed Jun. 30, 2020, (now U.S. Pat. No. 11,648,036), which is a continuation of U.S. patent application Ser. No. 15/351,530, filed Nov. 15, 2016, (now U.S. Pat. No. 10,695,096), which is a continuation of U.S. patent application Ser. No. 13/863,917, filed Apr. 16, 2013, (now U.S. Pat. No. 9,492,200), the entire disclosures of which are incorporated herein by reference.

FIELD

This disclosure relates to biological medical devices and methods, and particularly to biological medical suture systems and methods.

BACKGROUND

In many circumstances, it may be desirable to couple two or more bones or tissue segments together. For example, a bunion (hallux valgus) is a common deformity characterized by lateral deviation of the great toe (hallux) on the mesophalangeal joint (where the first metatarsal bone and hallux meet). One method of treating this deformity is to pull the great toe generally into proper alignment using a suture (or the like) disposed around the adjacent, pointer or index toe. In some applications, the two ends of the suture may need to be tied together. Additionally, torn or partially ligaments may be treated by suturing the ligament portions together. Unfortunately, many surgeons are uncomfortable tying knots because of the possibility of the knot becoming loose and/or the difficulty associated with tying a knot during a surgical procedure.

BRIEF DESCRIPTION OF THE DRAWINGS

Features and advantages of the present invention are set forth by description of embodiments consistent with the present invention, which description should be considered in conjunction with the accompanying drawings wherein:

FIG. 27 illustrates a bottom perspective view of the suture pin of FIGS. 24 and 25;

FIG. 28 illustrates a side view of the suture pin of FIGS. 24 and 25;

FIG. 29 illustrates a bottom view of the suture pin of FIGS. 24 and 25;

FIG. 30 illustrates an end view of the suture pin of FIGS. 24 and 25;

DETAILED DESCRIPTION

One embodiment of the present disclosure may feature suture systems and methods for coupling together two bones, bone segments, and/or tissue segments. The suture systems feature an all suture/thread construction which eliminates the need for the surgeon to tie knots during the surgical procedure.

By way of a brief overview explained in greater detail herein, one aspect of the present disclosure features a suture system which may be used for the treatment of hallux valgus (i.e., bunion); however, the suture system may also be used with other bones and/or may be used for the treatment of cracked and/or broken bone fragments. The suture system includes a suture construct having at least one reduction construct. The reduction construct includes a locking limb, a contractible loop, and an opposed loop disposed generally opposite to the contractible loop. The suture construct is configured to be selectively arranged in an expanded state/position and a reduced state/position. When in the expanded state/position, one or more of the contractible loops are passed through a respective passageway from through a first to the second bone or bone fragment until a portion of the contractible loop(s) extends beyond an opening in the second bone or bone fragment. A suture pin may be passed through the first (and optionally second contractible loop). To reduce/tighten the suture construct into the reduced state/position, the length/size of the opposed loop(s) is reduced thereby reducing the length/size of the first and second contractible loop(s) and biasing the first and second bones/bone fragments towards each other. Once the suture construct applies a desired amount of force to the bones/bone fragments in the reduced state, tension on the suture construct causes the opposed loop(s) to reduce against the locking limb(s), thereby locking, fixing, or otherwise securing the suture construct the reduced state.

Figure 1:
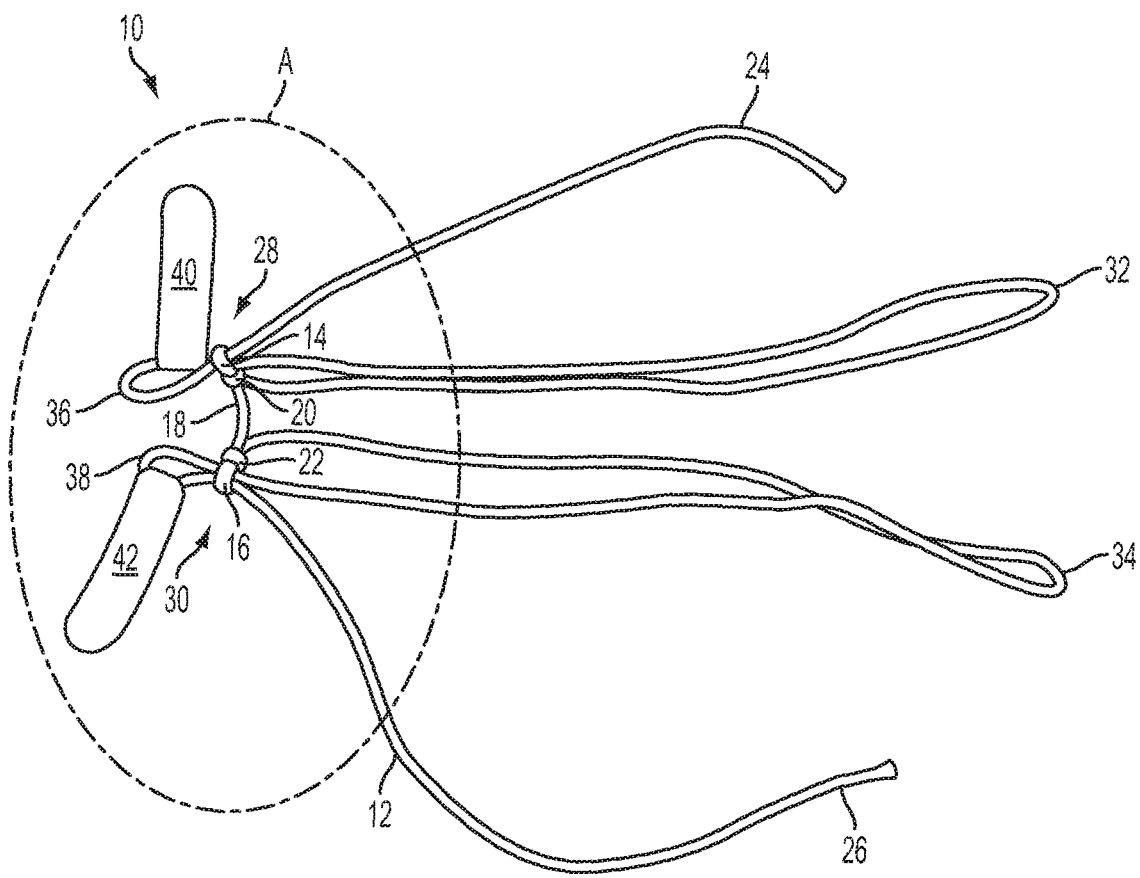
FIG. 1 is a plan view of one embodiment of a suture construct consistent with one embodiment of the present disclosure.

With reference to FIG. 1, one embodiment of a suture construct 10 is generally illustrated. The suture construct 10 includes one or more reduction constructs (e.g., a first and optionally a second reduction construct 28, 30). As explained herein, the first and the second reduction constructs 28, 30 (which may have the same or different configuration) are configured to be selectively reduced in size and locked, fixed, or otherwise secured in the reduced formation to apply a compressive force. While the suture construct 10 is illustrated having two reduction constructs 28, 30 separated by a bridge 18, it should be appreciated that a suture construct consistent with the present disclosure may include only one reduction construct 28.

The suture construct 10 may be formed from a single piece of suture 12, though it may also be formed from more than one piece of suture 12. The suture 12 may include woven and non-woven sutures, either of which may be formed from one or more threads or fibers. The threads/fibers may all be the same material or may include two or more different materials. The suture 12 may optionally include one or more coatings such as, but not limited to, antimicrobial materials to reduce potential infection. The suture 12 may include absorbable or non-absorbable materials. The diameter of the suture 12 will depend on the intended application; however, the suture 12 may include, but is not limited to, a #2, #3, #4 and/or #5 suture as defined by the United State Pharmacopeia (U.S.P.), for example, a #4 suture.

Figure 2:
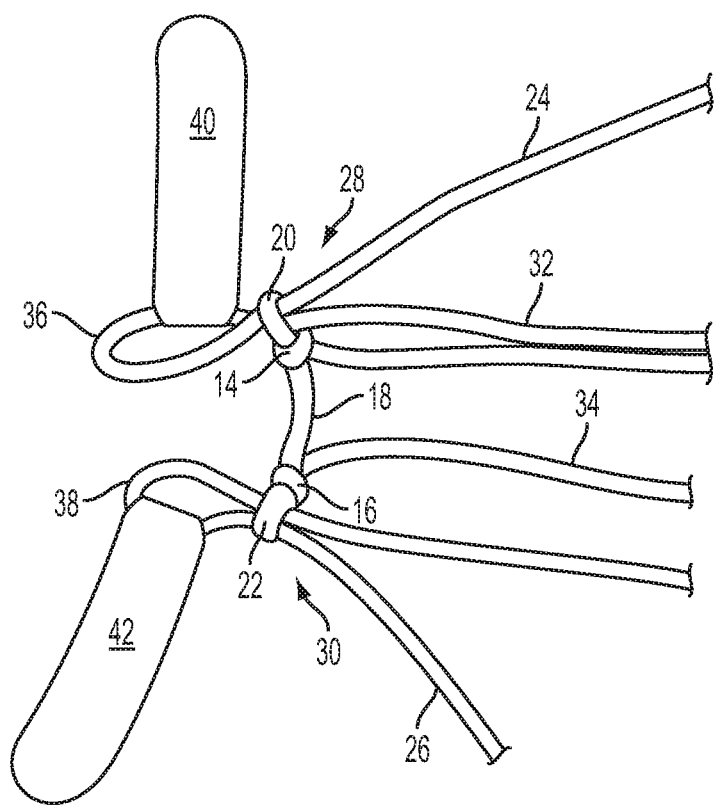
FIG. 2 is a close up of region A in FIG. 1.

With additional reference to FIG. 2 (which shows a close-up of region A in FIG. 1), the suture construct 10 includes the first and second reduction constructs 28, 30, each separated by a bridge 18. The first and second reduction constructs 28, 30 each include a first and a second knot 14, 16. The first and second knots 14, 16 may include any type of knot which can form a loop 20, 22, respectively. For example, one or more of the first and second knots 14, 16 may include splice (e.g., a sliding splice or the like), a slip knot, a running bowline, etc. Portions of the suture 12 are passed through a respective one of the loops 20, 22 to form the first and second reduction constructs 28, 30. The first and second reduction constructs 28, 30 each include a contractible loop 32, 34 and a opposed loop 36, 38, each of which are separated by the first and second loops 20, 22, respectively. A first portion of each of the opposed loops 36, 38 extends through the loops 20, 22 from the contractible loops 32, 34, respectively, and a second portion of each of the opposed loops 36, 38 extends through the loops 20, 22 and terminates at the first and second free ends 24, 26 of suture (also referred to as the first and second locking limbs 24, 26). A first portion of each of the contractible loops 32, 34 extends through the loops 20, 22 from the opposed loops 36, 38, respectively, and a second portion of each of the contractible loops 32, 34 extends from and terminates at the loops 20, 22.

Optionally, the first and second opposed loops 36, 38 may be temporarily retained in an expanded position (as generally illustrated in FIGS. 1 and 2) using a first and second tab 40, 42, respectively. The tabs 40, 42 may include, for example, folded pieces of metal (e.g., but not limited to, aluminum), plastic, suture, or the like configured to extend through the opposed loops 36, 38, thereby preventing the opposed loops 36, 38 from being pulled through the first and second loops 20, 22, respectively.

Figure 3:
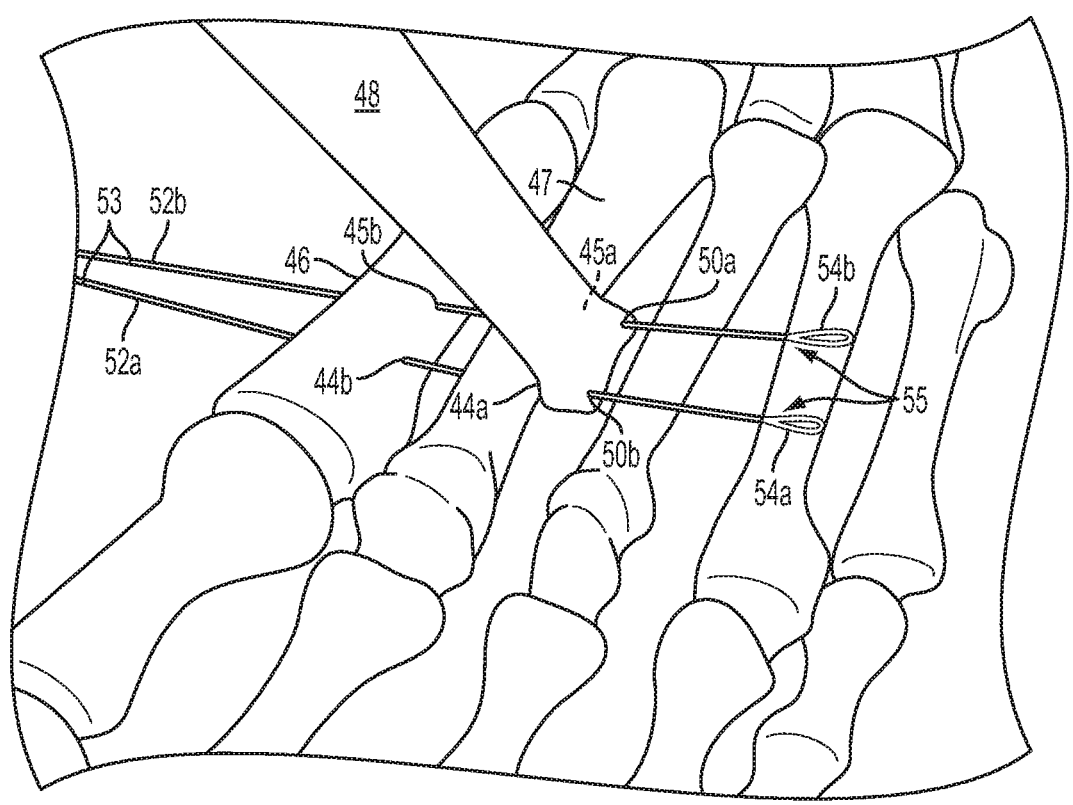
FIG. 3 illustrates one embodiment of forming the passageways through the bones consistent with the present disclosure.

Turning now to FIGS. 3-7, embodiments illustrating how the suture system can be used to treat a medical condition are generally illustrated. With reference to FIG. 3, two generally parallel passageways 44, 45 are drilled through a first and second bone 46, 47 (e.g., the first and second metatarsus bones 46, 47). A drill guide 48 may be used to form the passageways 44, 45. In particular, the drill guide 48 includes two drill bushings/openings 50a, 50b spaced apart from each other. The spacing of the bushings 50a, 50b is selected based on the size of the bones 46, 47 being drilled. In particular, the spacing may be selected such that the impact on the overall strength of the bones 46, 47 is minimized, thereby reducing the potential of damaging the bones 46, 47. By way of example, the spacing may be selected within the range of 6-10 mm. It should also be appreciated that the spacing between the first and second splices 14, 16 should generally correspond to the spacing of the bushings 50a, 50b.

In practice, the drill guide 48 may be placed against a portion of the second bone 47. A first passing pin or drill bit 52a (e.g., but not limited to, a 1.2 mm passing pin) is advanced through the first bushing 50a of the drill guide 48 to form a first second portions 44a, 44b (collectively referred to as the first passageway 44) in the first and second bones 46, 47, respectively. Similarly, a second passing pin or drill bit 52b is advanced through the second bushing 50b of the drill guide 48 to form a first second portions 45a, 45b (collectively referred to as the second passageway 45) in the first and second bones 46, 47, respectively. The distal ends 53 of the first and second drill bits 52a, 52b extend beyond the first bone 46 and the proximal ends 55 have not passed through the second bone 47. The first and second drill bits 52a, 52b optionally include a loop or snare 54a, 54b extending from the proximal ends 55.

Figure 4:
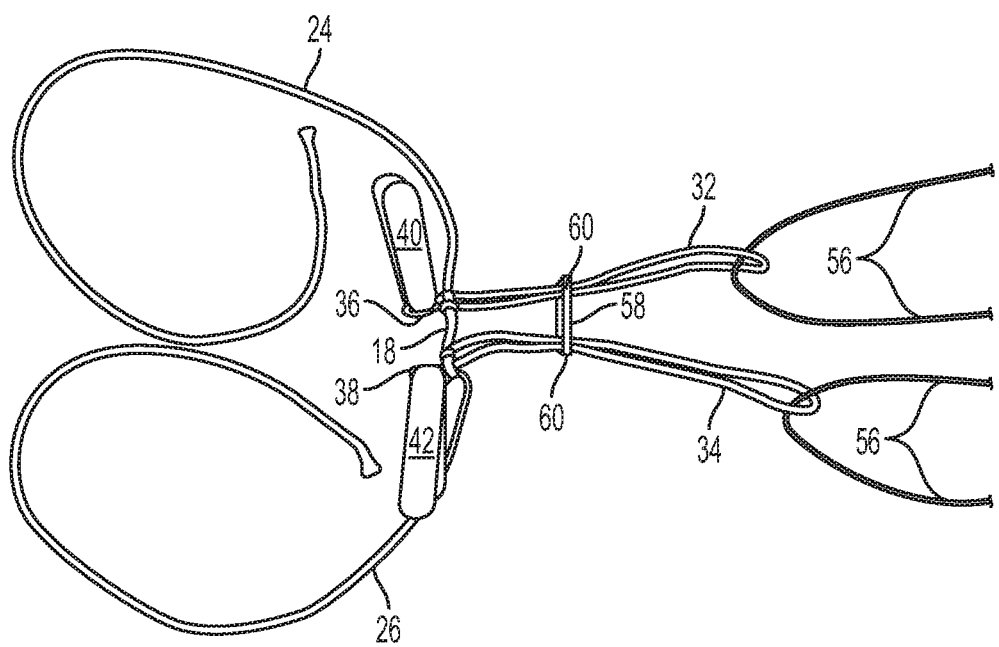
FIG. 4 illustrates one embodiment of the suture construct in combination with pull strands consistent with the present disclosure.

With the passageways 44, 45 having been formed, the suture construct 10 may then be advanced through the passageways 44, 45. Turning now to FIG. 4, the suture construct 10 is illustrated in combination with two pull strands 56. The pull strands 56 are disposed around a distal end of the first and second contractible loops 32, 34 and are configured to be releasably coupled to the first and second contractible loops 32, 34. For example, the pull strands 56 may include a loop disposed around the first and second contractible loops 32, 34. The pull strands 56 may also be tied or otherwise releasably secured to the first and second contractible loops 32, 34. Optionally, the suture construct 10 includes a suture plate 58. The suture plate 58 includes two apertures 60 spaced apart a distance generally corresponding to the distance between the two passageways 44, 45 and the spacing of the first and second knots 14, 16. The suture plates 58 may have a "FIG. 8" cross-section or may have a generally rectangular cross-section.

Figure 5:
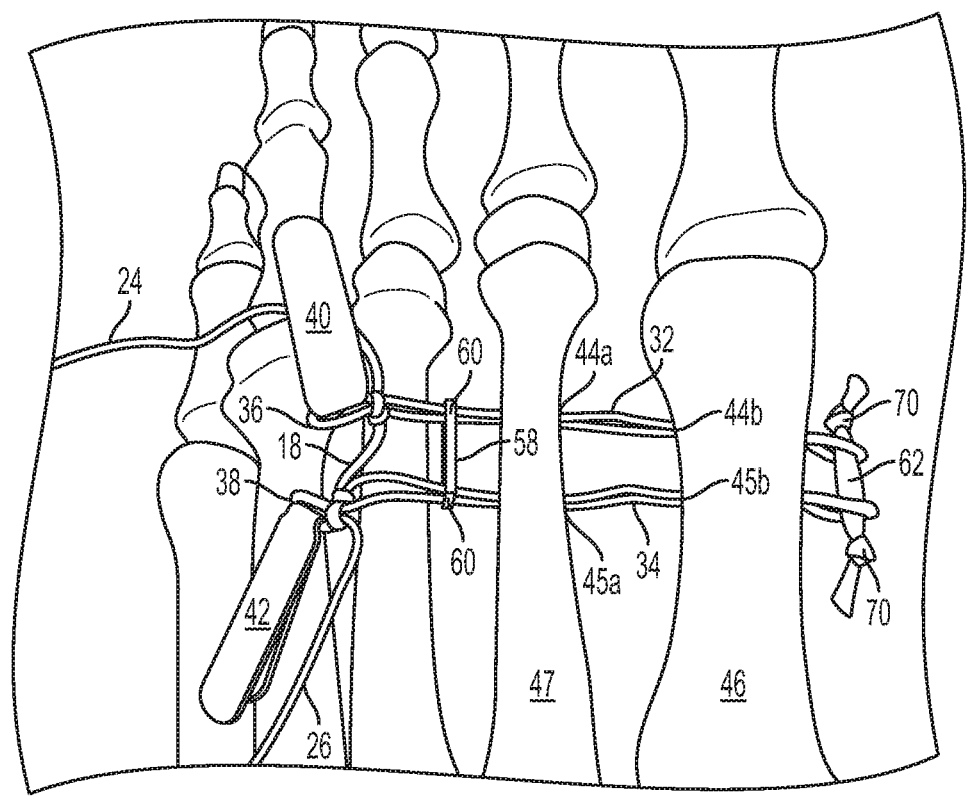
FIG. 5 illustrates the suture construct disposed within the passageways in the bone consistent with at least one embodiment of the present disclosure.
Figure 6:
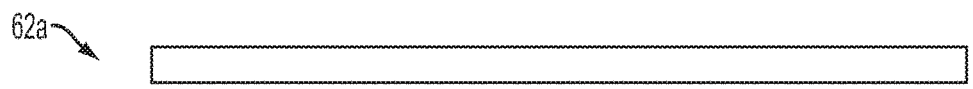
FIGS. 6-12 illustrate various embodiments of suture pins consistent with the present disclosure.

With reference to FIGS. 3, 4, and 5, the pull strands 56 are configured to be coupled to the loops/snares 54a, 54b extending from the drill bits 52a, 52b. The drill bits 52a, 52b are then retracted through the passageways 44, 45, thereby advancing the pull strands 56 through the passageways 44, 45. Once the pull strands 56 are beyond the first bone 46, the pull strands 56 can be used to pull/advance a portion of the contractible loops 32, 34 through a respective one of the passageways 44, 45 (from the second bone 47 and then through the first bone 46) until a distal portion of the contractible loops 32, 34 extends beyond the first bone 46. The contractible loops 32, 34 may be advanced through the passageways 44, 45 until the bridge 18 (or the optional suture plate 58) is proximate to or abuts against the second bone 47, thereafter the pull strands 56 may be disconnected/released from the first and second contractible loop 32, 34 as generally illustrated in FIG. 5.

With the first and second contractible loops 32, 34 advanced through the passageways 44, 45, the suture pin 62 (FIG. 5) is then coupled to the first and second contractible loop 32, 34 such that the suture construct 10 forms an enclosed loop extending around a portion of the first and second bones 46, 47. The enclosed loop suture construct is defined by the first and second contractible loops 32, 34, the bridge 18, and the suture pin 62. According to one embodiment, the suture pin 62 is passed through the first and second contractible loops 32, 34 such that a portion of the first and second contractible loops 32, 34 is disposed around a portion of the suture pin 62. Alternatively (or in addition), the suture pin 62 may be secured to the first and second contractible loops 32, 34 using one or more fasteners, clamps, or the like.

The suture pin 62 may have a length larger than the spacing between the two passageways 44, 45 in the first bone 46. Having the length of the suture pin 62 greater than the spacing between the two passageways 44, 45 in the first bone 46 allows the first and second contractible loops 32, 34 to extend substantially parallel to the two passageways 44, 45, thereby minimizing stress placed on the bones 46, 47 by the first and second contractible loops 32, 34. For example, if the first and second contractible loops 32, 34 are not parallel to the passageways 44, 45, then the first and second contractible loops 32, 34 will exert a force against the sideways of the passageways 44, 45 and/or the portion of bone between the passageways 44, 45, causing the first and second contractible loops 32, 34 to dig into and damage the bones 46, 47.

In addition to having a length greater than the spacing between the two passageways 44, 45 in the first bone 46, the suture pin 62 may also have an overall width, diameter, or cross-section that is greater than the diameter of the passageways 44, 45 such that the suture pin 62 will not fit within the passageways 44, 45. As explained herein, the suture pin 62 consistent with the present disclosure may be coupled to the first and second contractible loops 32, 34 after the first and second contractible loops 32, 34 have been advanced through the passageways 44, 45. As a result, the suture pin 62 does not need to be advanced through the passageways 44, 45 and diameter of the passageways 44, 45 may be minimized (i.e., the diameter of the passageways 44, 45 need only be slightly larger than the overall cross-section of the first and second contractible loops 32, 34). As may be appreciated, the smaller diameter of the passageways 44, 45 minimizes the negative impact on the strength of the bones 46, 47 by reducing the amount of bone material that is removed.

Turning now to FIGS. 6-12, various embodiments of the suture pin 62 are generally illustrated. For example, FIG. 6 generally illustrates a suture pin 62a having a generally elongated shape. The suture pin 62a may be formed from metal (e.g., but not limited to, stainless steel, titanium, aluminum, chromium cobalt, and/or any alloy thereof), plastic (e.g., but not limited to, polyether ether ketone (PEEK), polyethylene (PE) such as ultrahigh molecular weight polyethylene (UHMWPE) and high density polyethylene (HDPE), or the like), composite materials (e.g., reinforced plastics such as fiber-reinforced polymers, metal composites, ceramic composites, or the like), sutures (woven and/or non-woven suture), or the like. The suture pin 62a may have a generally consistent cross-section throughout its length. The suture pin 62a may have a generally circular cross-section and/or may have a non-circular cross-section (e.g., rectangular, oval, or the like).

Figure 7:
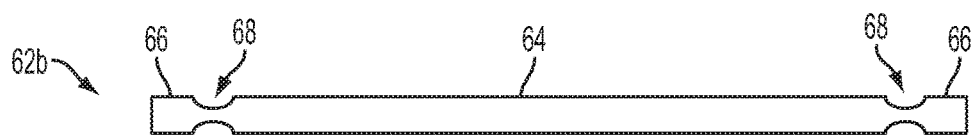

With reference to FIG. 7, a suture pin 62b is illustrated having a main body 64, an end region 66, and at least one reduced portion 68 having a smaller cross-section compared to the main body 64 and/or the end region 66. The reduced portion 68 may include a groove, slot, channel, or the like configured to aid in locating the first and second contractible loops 32, 34 with respect to the suture pin 66b, and aid in preventing the suture pin 62b from becoming dislodged with respect to the first and second contractible loops 32, 34 (i.e., aid in securing the first and second contractible loops 32, 34 with respect to the reduced portion 68). The reduced portions 68 may extend radially around only a portion of the suture pin 62b (e.g., 180 degrees around, 90 degrees around, or the like) or may extend radially around the entire cross-section of the suture pin 62b. The positions of the reduced portions 68 may be separated from each other a distance generally corresponding to the distance between the two passageways 44, 45 and the spacing of the first and second splices 14, 16. While the suture pin 62b is illustrated having two reduced portions 68, it should be appreciated that the suture pin 62b may include only one or may include more than two reduced portions 68 which are distributed along the length of the suture pin 62b. Having more than two reduced portions 68 may allow the suture pin 62b to be used to different suture constructs 10 having different spacing between the first and second splices 14, 16.

As generally illustrated in FIGS. 8-12, a suture pin 62 consistent with the present disclosure may also include one or more enlarged portions configured to aid in locating the first and second contractible loops 32, 34 with respect to the suture pin 66, and aid in preventing the suture pin 62 from becoming dislodged with respect to the first and second contractible loops 32, 34 (i.e., aid in securing the first and second contractible loops 32, 34 with respect to the enlarged portions). The enlarged portions may be separated from each other a distance which is generally equal to or greater than the distance between the two passageways 44, 45 and the spacing of the first and second splices 14, 16.

Figure 8:
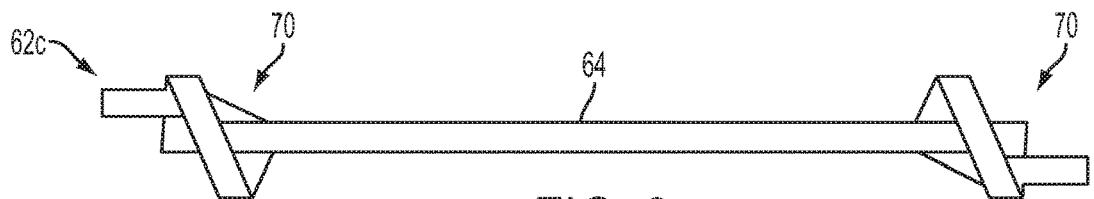

One embodiment of a suture pin 62c having an enlarged portion is generally illustrated in FIG. 8. More specifically, the suture pin 62c is formed from one or more pieces of suture (either woven or non-woven suture). The suture pin 62c includes enlarged portions 70 disposed at generally opposite end regions of a main body 64. The enlarged portions 70 have a cross-section that is larger than the cross-section of the main body 64. The overall width, diameter, or cross-section of the enlarged portions 70 may also be greater than the diameter of the passageways 44, 45 such that the suture pin 62c will not fit within the passageways 44, 45.

The enlarged portions 70 may be formed by forming one or more knots (such as, but not limited to, an overhand knot, half hitch knot, square knot, half knot, or the like). The knots may be made from the same piece of suture as the main body 64, and/or may include additional pieces of suture. A benefit to a suture pin having an all-suture construction is that is minimizes the amount of different materials used by the suture system. Additionally, tissue may grow into the suture material, thereby reducing the possibility of the suture pin 62c from migrating with respect to the first and second contractible loops 32, 34.

Figure 9:
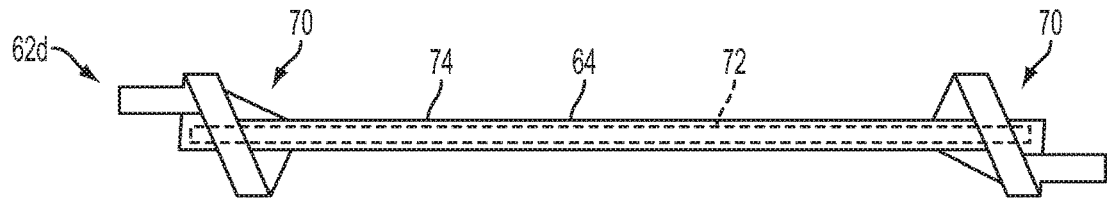

Another embodiment of a suture pin 62d having enlarged portions 70 is generally illustrated in FIG. 9. The suture pin 62d may be similar to the suture pin 62c, however, the suture pin 62d includes a rigid element/member 72 over which the suture 74 is woven, tied, or otherwise secured around. For example, the rigid element 72 may include an elongated member (e.g., a pin or the like as generally described in FIGS. 6, 7, and 10-12). The combination of the rigid element 72 and the suture element 74 may increase the structural rigidity of the suture pin 62d, thereby facilitating the assembly of the suture system during the surgical procedure.

Additionally, the combination of the rigid element 72 and the suture element 74 may increase the overall strength of the suture pin 62d, and may also allow for tissue growth into the suture element 74 as discussed herein.

Figure 10:
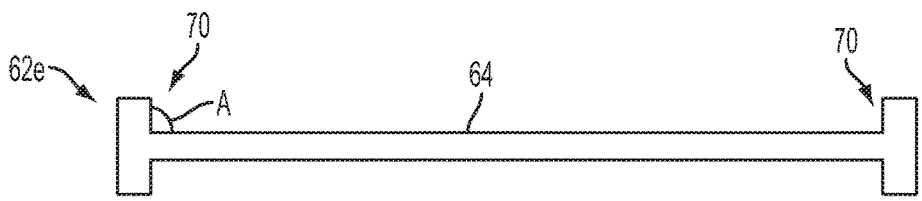
Figure 11:
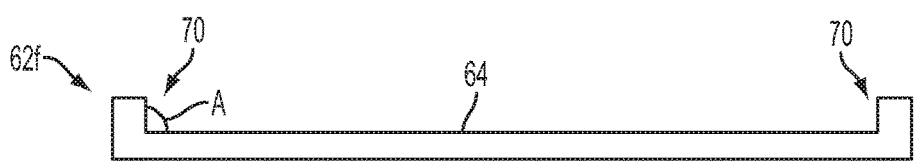
Figure 12:
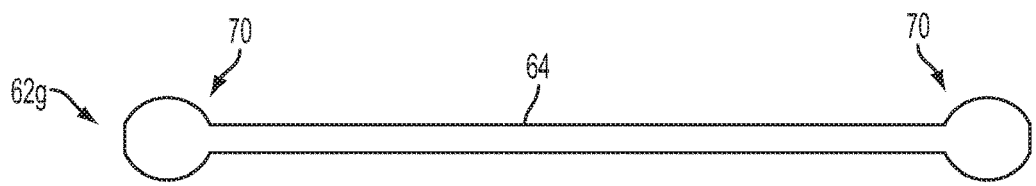

Other embodiments of a suture pin 62e-62g having enlarged portions 70 are generally illustrated in FIGS. 10-12. The suture pins 62e-62g include a generally elongated main body 64 having enlarged portions 70 disposed about the proximal end regions. The main body 64 and the enlarged portions 70 may be formed as an integral component (e.g., pieces bonded together, which may be made from the same or different materials) or may be formed as a unitary component (i.e., formed as a single component from the same material). The suture pins 62e-62g may be formed from metal (e.g., but not limited to, stainless steel, titanium, aluminum, chromium cobalt, and/or any alloy thereof), plastic (e.g., but not limited to, polyether ether ketone (PEEK), polyethylene (PE) such as ultrahigh molecular weight polyethylene (UHMWPE) and high density polyethylene (HDPE), or the like), or composite materials (e.g., reinforced plastics such as fiber-reinforced polymers, metal composites, ceramic composites, or the like).

The enlarged portions 70 may have a generally "T" shaped or disc-shaped protrusion extending generally radially outward as generally illustrated in FIG. 10 or a may have a generally "L" shaped protrusion extending generally radially outward as generally illustrated in FIG. 11. While the protrusions are illustrated extending radially outward at approximately 90 degrees from the body portion 64, it should be appreciated that the protrusions may extend radially outwardly at an angle A from the body portion 64 in the range of 10 degrees to 170 degrees. Additionally, while the protrusions are illustrated having a generally planar or linear shape, it should be understood that the protrusions may have a non-linear or non-planar shape such as a curved or arcuate shape. The enlarged portions 70 may also have a generally circular or cross-section, spherical shape, and/or may have a non-circular cross-section (e.g., rectangular, oval, or the like) as generally illustrated in FIG. 12.

Figure 13:
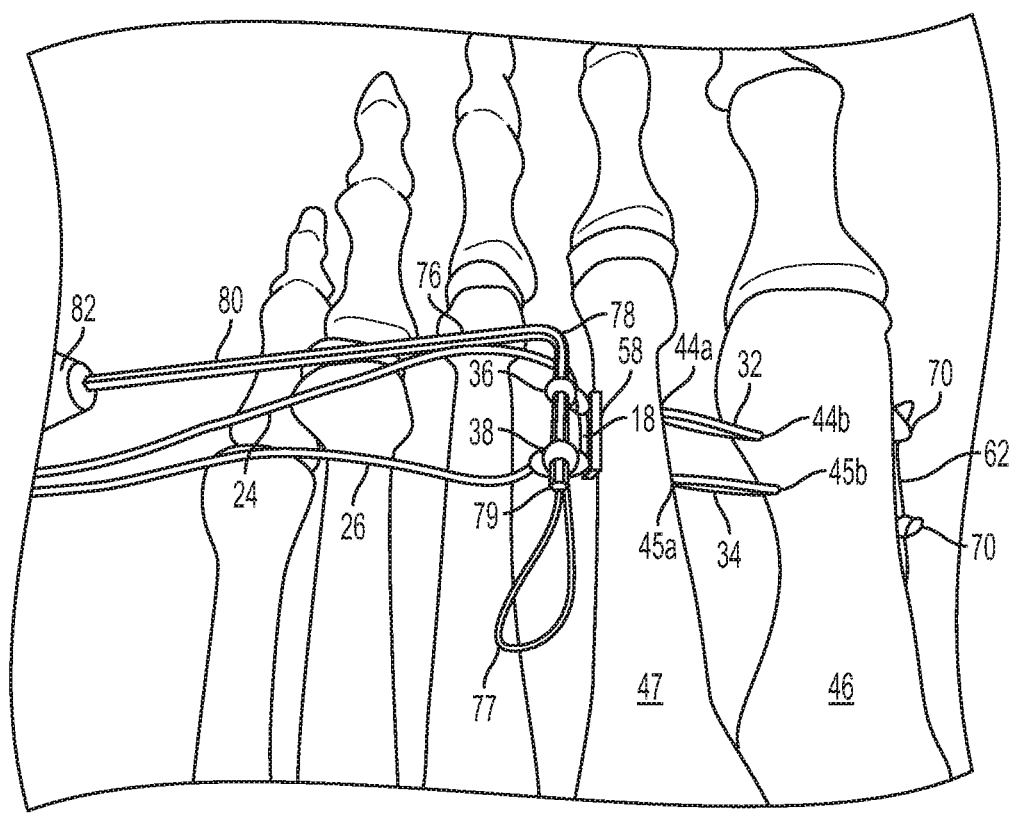
FIG. 13 illustrates one embodiment of the suture construct in combination with one embodiment of a pusher consistent with the present disclosure.

Turning back to FIG. 5, with the suture pin 62 extending between the first and second contractible loops 32, 34, the first and second contractible loops 32, 34 may be pulled away from the first bone 46 to urge the suture pin 62 against the first bone 46, thereby aiding in maintaining the suture pin 62 within the first and second contractible loops 32, 34. The first and second tabs 40, 42 are removed from the first and second opposed loops 36, 38 and a pusher 76 is advanced through the first and second opposed loops 36, 38 as generally illustrated in FIG. 13.

The pusher 76 is configured to aid in reducing/tightening the suture system and to urge the first and second bones 46, 47 towards each other. According to one embodiment, the pusher 76 includes a pivoting section 78 which is advanced through the first and second opposed loops 36, 38 and a pull snare 77 extending outward beyond the distal end 79 of the pivoting section 78. The pivoting section 78 optionally extends at an angle from an arm section 80. While the angle between the pivoting section 78 and the arm section 80 is illustrated at approximately 90 degrees, it should be appreciated that the angle therebetween will depend on the application and the surgeon's preference and may, for example, be in the range of 45 to 135 degrees. The pusher 76 also optionally includes a handle portion 82 coupled to the arm section 80 to aid in gripping the pusher 76.

To reduce/tighten the suture system, the surgeon pulls the locking limbs 24, 26 of the suture construct 10 away from the second bone 47 while simultaneously urging the pusher 76 towards the second bone 47, thereby reducing the length of the first and second contractible loops 32, 34 and applying a compressive force through the first and second contractible loops 32, 34, the bridge 18 (and the optional suture plate 58), and suture pin 62 to bias the first and second bones 46, 47 towards each other. More specifically, the length of the locking limbs 24, 26 of the suture construct 10 is extended as a portion of the suture 12 is pulled from the first and second contractible loops 32, 34 and through the opposed loops 36, 38. The pusher 76 prevents the opposed loops 36, 38 from self-collapsing as the locking limbs 24, 26 are pulled and effectively acts as a pulley.

Figure 14:
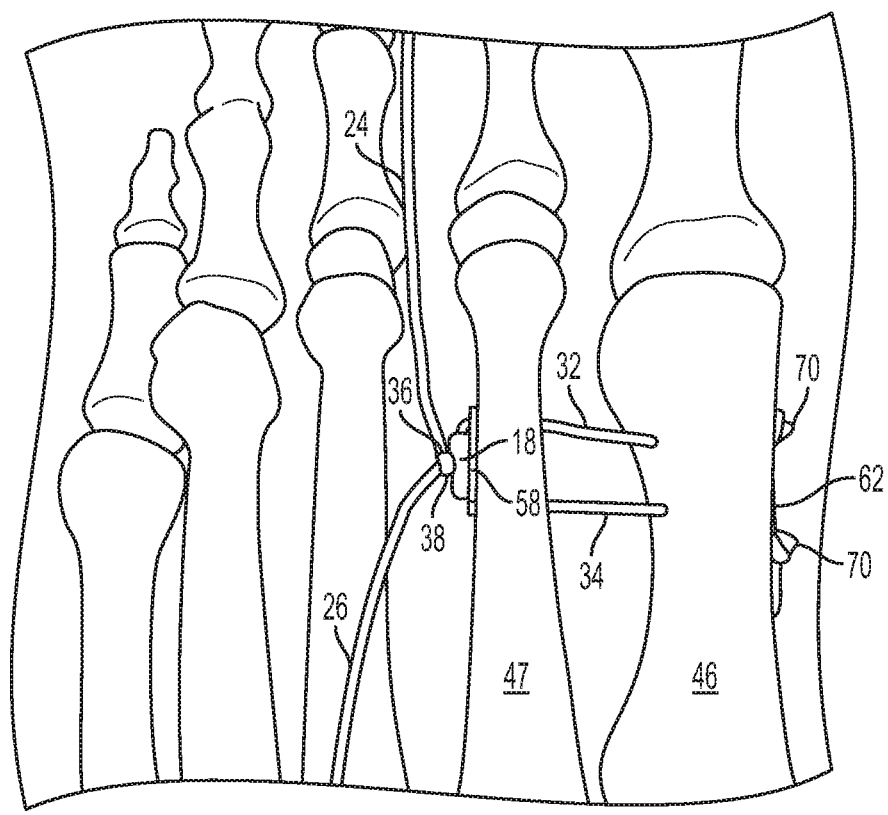
FIG. 14 illustrates the suture construct in a locked state consistent with at least one embodiment of the present disclosure.

Once the suture system applies a desired amount of force to urge the first and second bones 46, 47 towards each other, the locking limbs 24, 26 of the suture construct 10 are advanced into and captured by the pull snare 77 extending out from the distal end 79 of the pusher 76. The pusher 76 is then retracted through the first and second opposed loops 36, 38, causing a least a portion of the locking limbs 24, 26 to pass through the opposed loops 36, 38 as generally illustrated in FIG. 14. The tension on the suture construct 10 causes the opposed loops 36, 38 to reduce against the locking limbs 24, 26, thereby locking the suture construct 10 and preventing the suture construct 10 from loosening. Once the suture construct 10 is locked, excess lengths of the locking limbs 24, 26 may be trimmed proximate to the opposed loops 36, 38.

Figure 15:
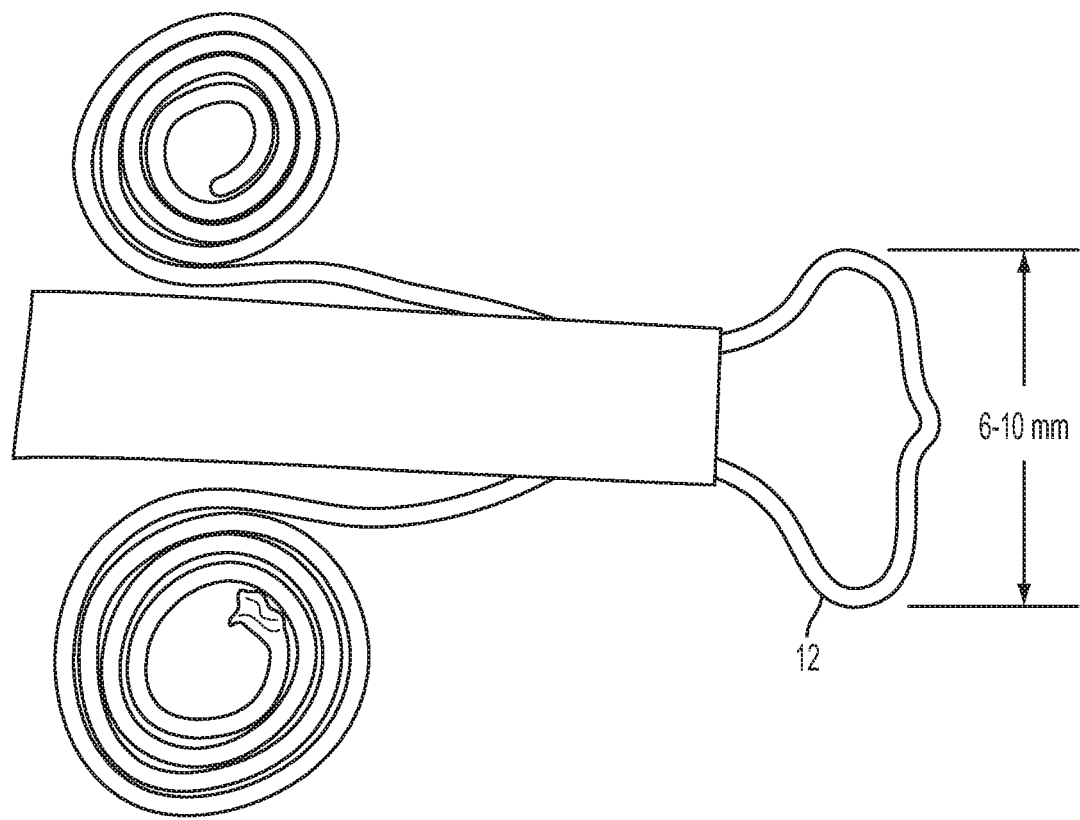
FIGS. 15-18 illustrate various steps for forming a suture construct consistent with at least one embodiment of the present disclosure.
Figure 16:
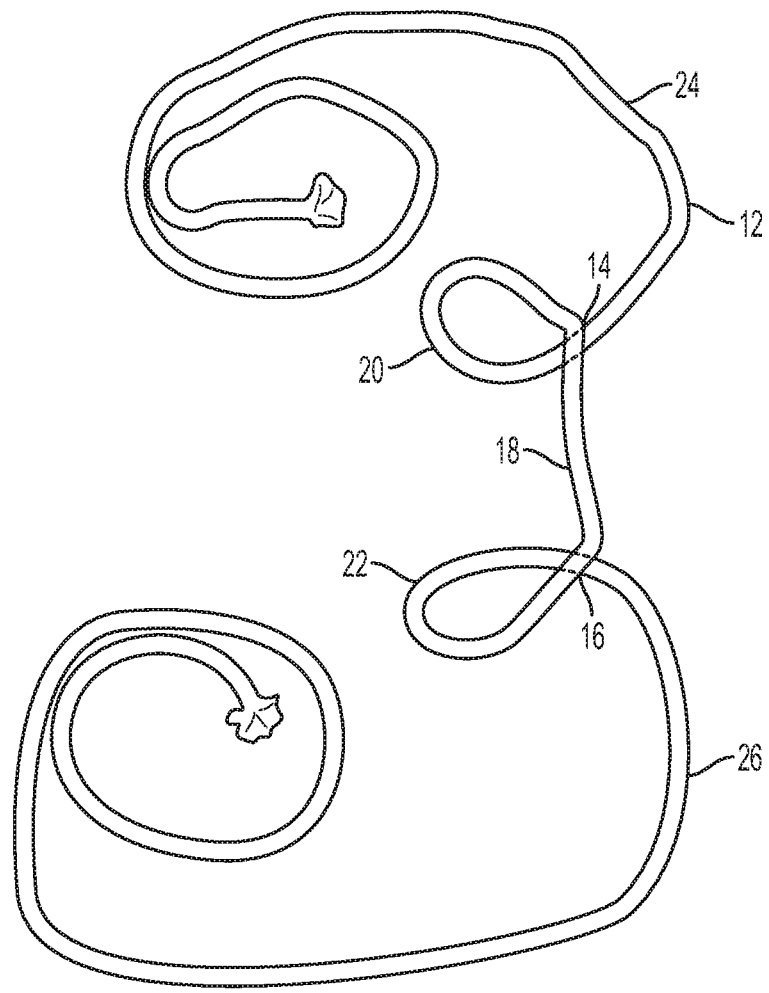
Figure 17:
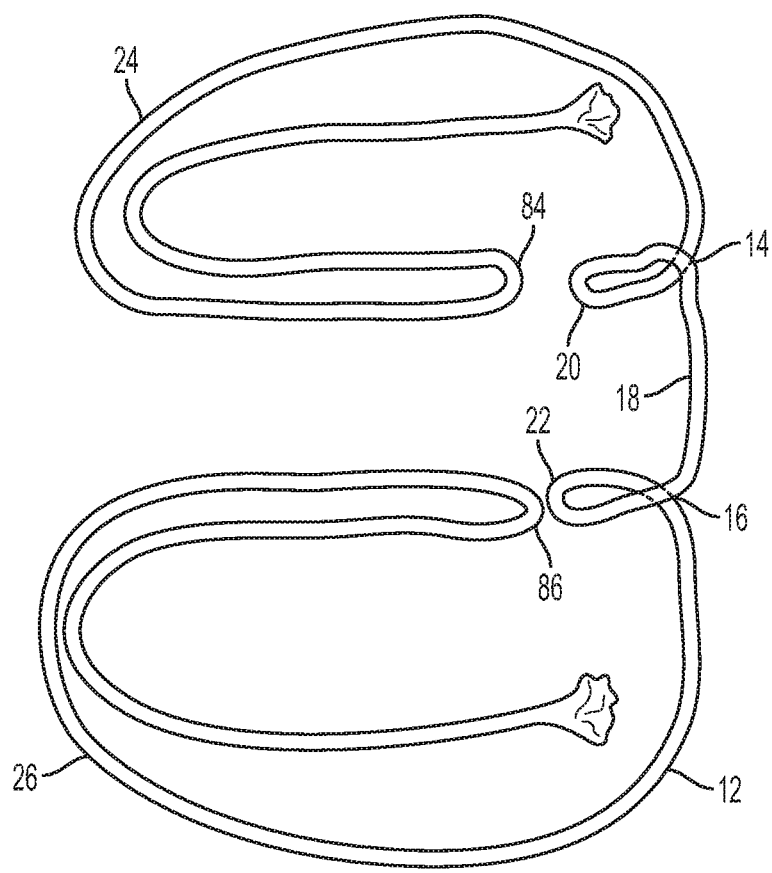
Figure 18:
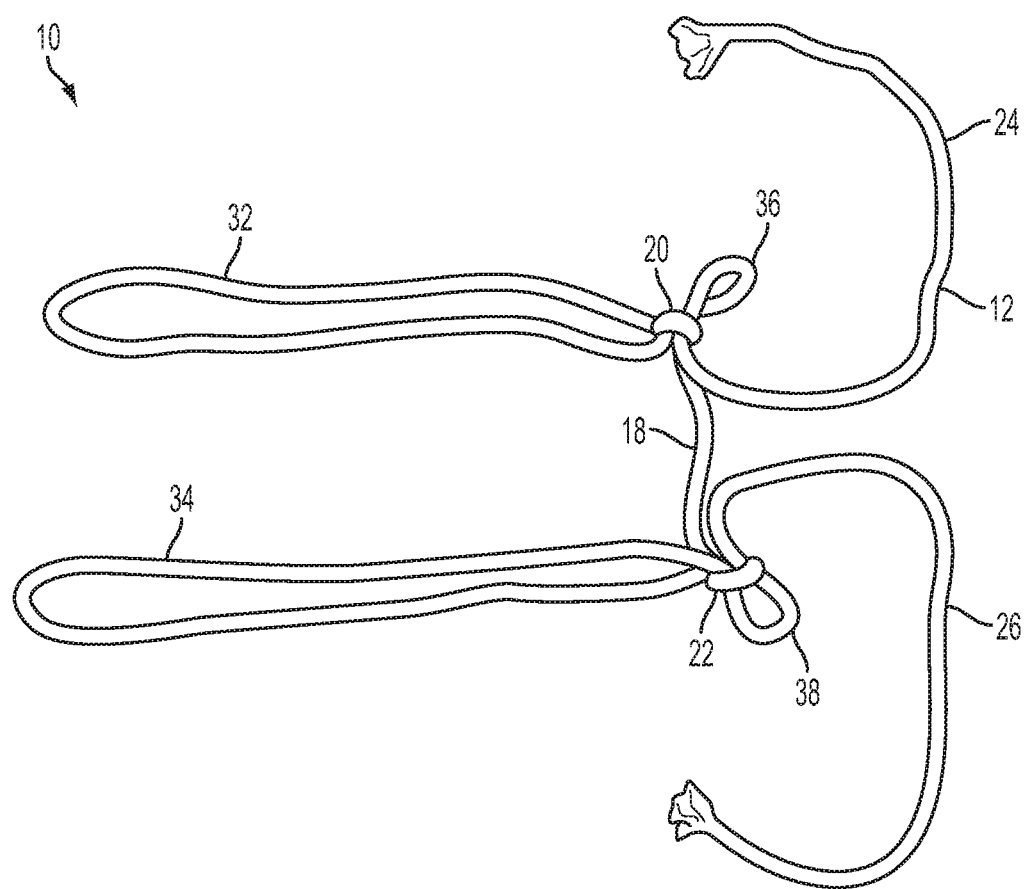

Turning now to FIGS. 15-18, the steps for forming one embodiment of a suture construct 10 consistent with one embodiment of the present disclosure is generally illustrated. With reference to FIG. 15, a length of suture 12 is provided and the spacing between the first and second knots 14, 16 is determined based on the desired spacing between the first and second passageways 44, 45. Turning now to FIG. 16, the first and second knots 14, 16 are formed in the suture 12 (for example, but not limited to, using any splicing technique known to those skilled in the art) and are separated by the bridge 18. The first and second loops 20, 22 are also formed as a result of forming the first and second knots 14, 16, respectively. Intermediate portions 84, 86, FIG. 17, of the suture 12 are then passed through the first and second loops 20, 22 to form the first and second contractible loops 32, 34 and the first and second opposed loops 36, 38 as generally illustrated in FIG. 18.

Figure 19:
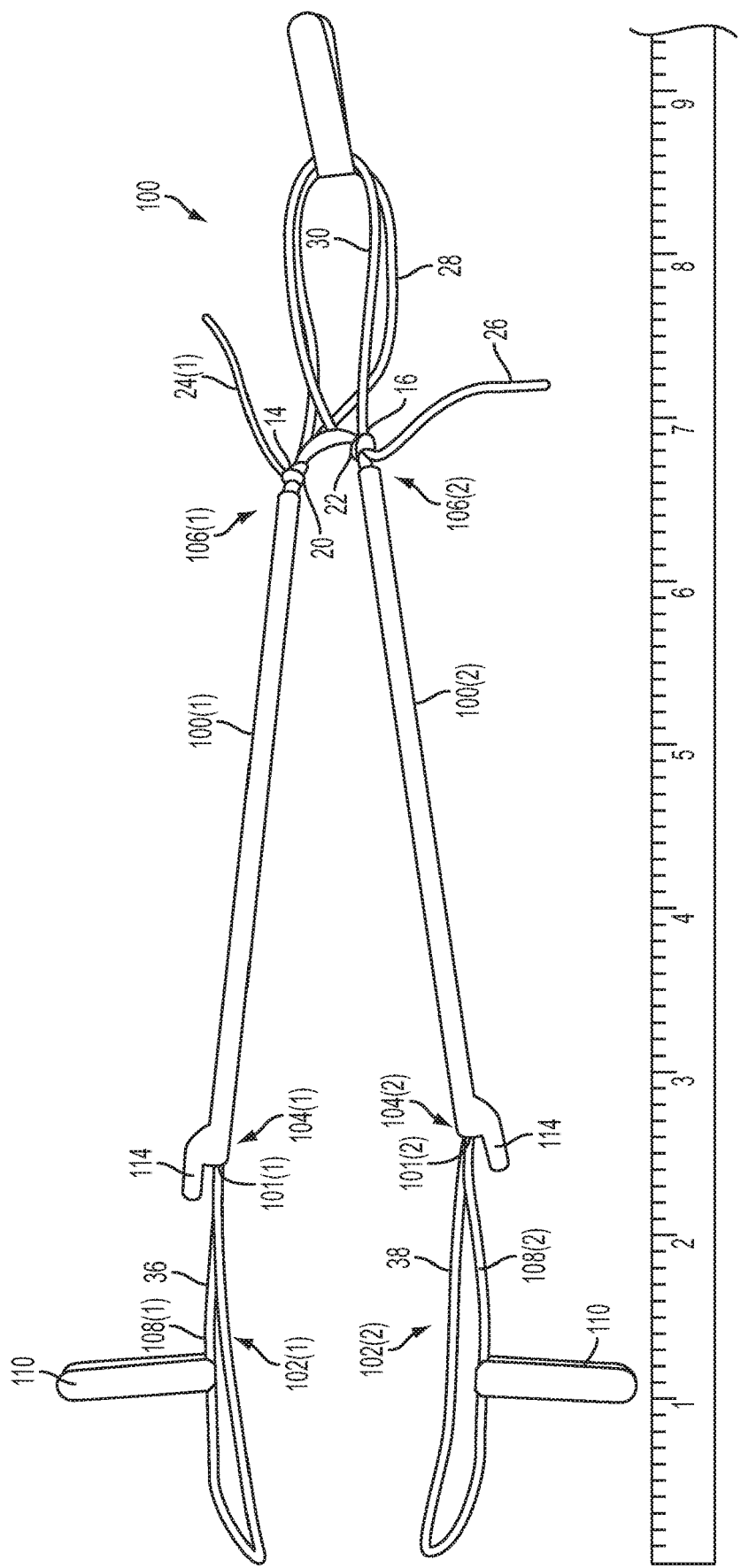
FIG. 19 illustrates another embodiment of suture system.

With reference to FIG. 19, another embodiment of a suture system 1a is generally illustrated. The suture system 1a includes a suture construct 10a, a first and a second pusher tubes 100(1), 100(2), a suture pin 62 (not shown for clarity), and optionally a suture plate 58 (also not shown for clarity). The suture construct 10a is similar to the suture construct 10 described herein, except that the first and second opposed loops 36, 38 have been lengthened, the locking limbs 24, 26 of the suture 12 have been advanced through the opposed loops 36, 38, and the lumens 101(1), 101(2) of the pusher tubes 100(1), 100(2) have been advanced over a portion of the opposed loops 36, 38 such that a distal portion 102(1), 102(2) of the opposed loops 36, 38 extends beyond a distal end 104(1), 104(2) of the pusher tubes 100(1), 100(2). The proximal ends 106(1), 106(2) of the pusher tubes 100(1), 100(2) are proximate to and/or abuts against the splice snares 20, 22 and/or the splices 14, 16, respectively. Optionally, the "hot side" 108(1), 108(2) of the opposed loops 36, 38 may be marked, for example, using one or more marking indicia, tabs 110 or the like. As used herein, the term "hot sides" of the opposed loops 36, 38 refers to the portions of the opposed loops 36, 38 which pass through the first and second loops 20, 22 from the first and second contractible loops 32, 34 when the first and second contractible loops 32, 34 are reduced in size.

The suture construct 10a of the system 1a is installed in the first and second bones 46, 47 in a manner similar to the suture construct 10. For the sake of brevity, all of the installation steps of the suture system 1a have not been repeated, and reference is made to the remainder of the instant application. Specifically, the passageways 44, 45 may be formed in the bones 46, 47 and the contractible loops 32, 34 are advanced through a respective one of the passageways 44, 45 (from the second bone 47 and then through the first bone 46) until a distal portion of the contractible loops 32, 34 extends beyond the first bone 46 in the same manner as described herein. The contractible loops 32, 34 may be advanced through the passageways 44, 45 until the bridge 18 (or the optional suture plate 58) is proximate to or abuts against the second bone 47. With the first and second contractible loops 32, 34 advanced through the passageways 44, 45, a suture pin 62 is then coupled to the first and second contractible loops 32, 34 such that the suture construct 10 forms an enclosed loop extending around a portion of the first and second bones 46, 47 in the same manner described herein. With the suture pin 62 extending between the first and second contractible loops 32, 34, the first and second contractible loops 32, 34 may be pulled away from the first bone 46 to urge the suture pin 62 against the first bone 46, thereby aiding in maintaining the suture pin 62 within the first and second contractible loops 32, 34.

Figure 20:
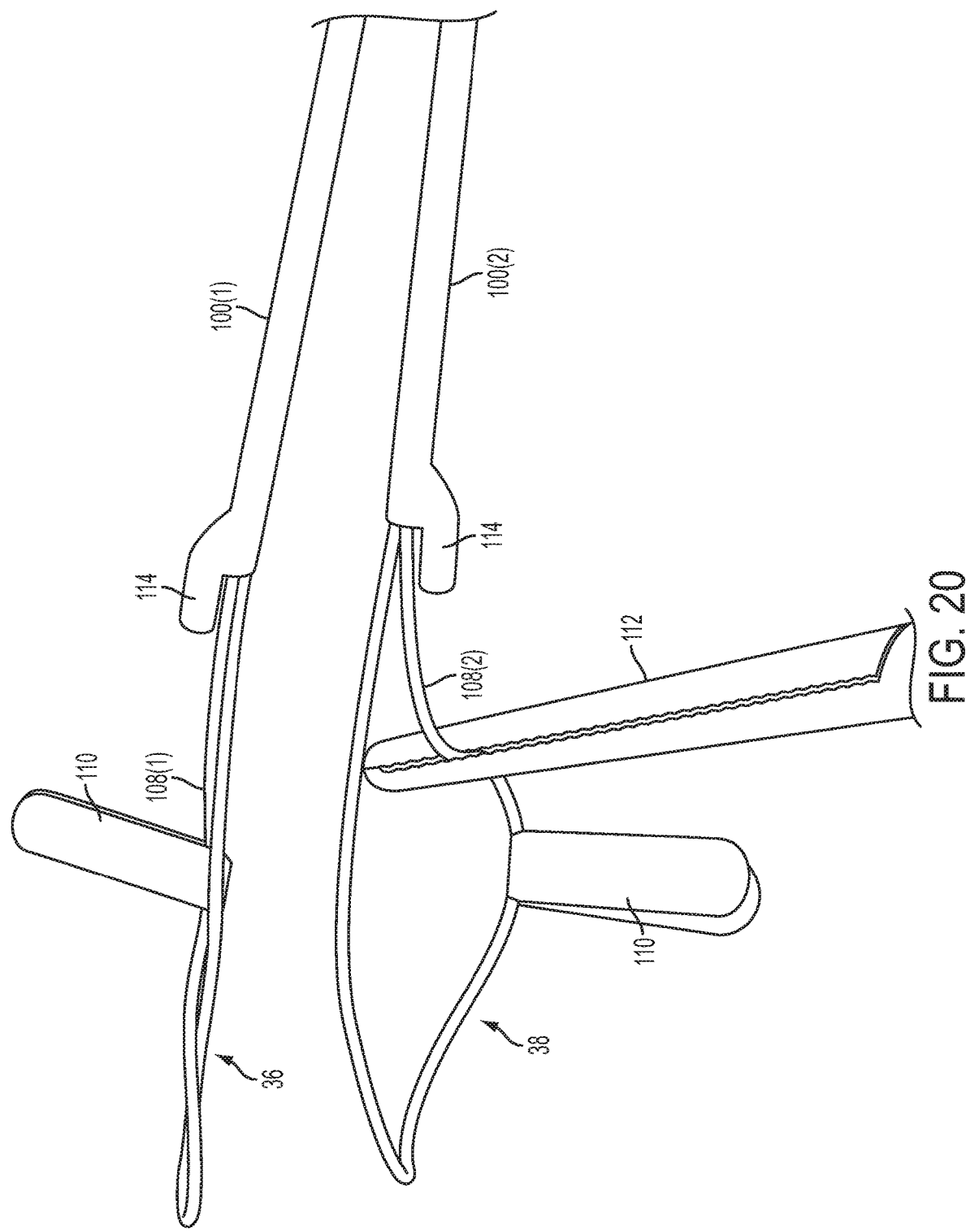
FIGS. 20 and 21 illustrate installation/reduction steps corresponding to the suture system illustrated in FIG. 19.
Figure 21:
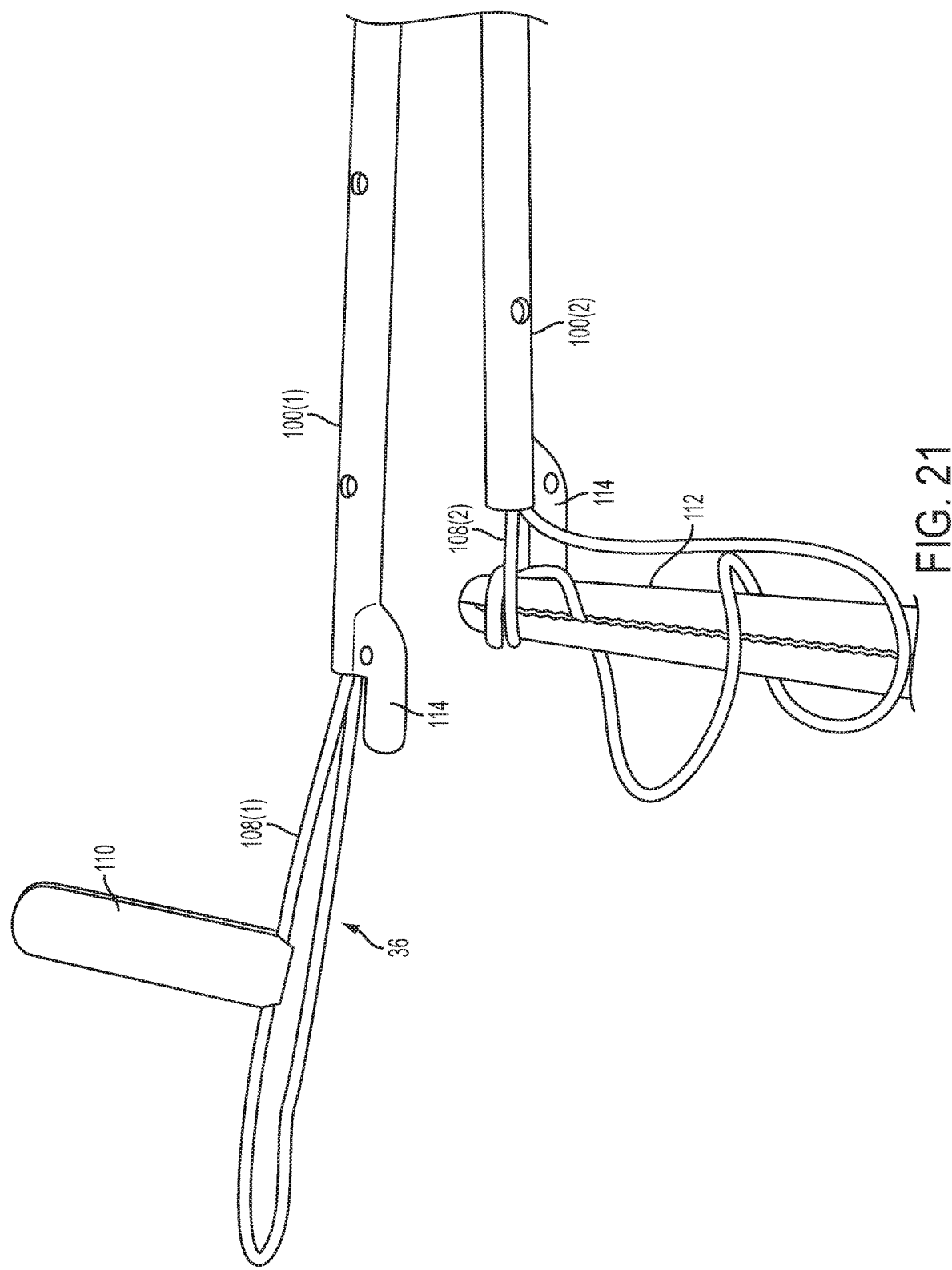

Whereas the reduction of the suture construct 10 utilized a pusher 76, the installation and reduction of the suture construct 10a replaces the pusher 76 and utilizes one or more pusher tubes 100(1), 100(2) instead. More specifically, with the suture pin 62 extending between the first and second contractible loops 32, 34 and urged against the first bone 46, the user grasps the hot sides 108(1), 108(2) (for example, using a gripper, grasper, forceps, 112 or the like as generally illustrated in FIG. 20) of the opposed loops 36, 38 and pulls the hot sides hot sides 108(1), 108(2) through the pusher tubes 100(1), 100(2) and distally or away from the contractible loops 32, 34 (for example, but not limited to, rotating or twisting the forceps 112 against a distal end 104(1), 104(2) of the pusher tubes 100(1), 100(2) as generally illustrated in FIG. 21). The pusher tubes 100(1), 100(2) may have a length sufficient to allow the surgeon to operate on the distal ends 104(1), 104(2) outside of the patient's tissue.

As may be appreciated, pulling the hot sides 108(1), 108(2) of the opposed loops 36, 38 causes the length of the contractible loops 32, 34 to be reduced since the hot sides 108(1), 108(2) are slidably coupled to the contractible loops 32, 34 through the loops 20, 22. Reducing the lengths of the opposed loops 36, 38 applies a compressive force through the first and second contractible loops 32, 34, the bridge 18 (and the optional suture plate 58), and suture pin 62 to bias the first and second bones 46, 47 towards each other. Once the desired amount of compressive force is applied to the bones 46, 47, the suture construct 10a may be temporally maintained in the compressed state by urging the pusher tubes 100(1), 100(2) against the loops 20, 22 and/or the knots 14, 16, and the tension on the hot sides 108(1), 108(2) (e.g., by means of the forceps 112) may be temporarily eliminated. While urging the pusher tubes 100(1), 100(2) against the loops 20, 22 and/or the knots 14, 16, the user may then pull on the locking limbs 24, 26 of the suture construct 10a. As noted above, the locking limbs 24, 26 are already passed through the opposed loops 36, 38. As the user pulls on the locking limbs 24, 26, the length of the opposed loops 36, 38 decreases until the opposed loops 36, 38 are compressed against the locking limbs 24, 26 extending therethrough. The tension on the suture construct 10a causes the opposed loops 36, 38 to reduce against the locking limbs 24, 26, thereby locking the suture construct 10a and preventing the suture construct 10a from loosening. Once the suture construct 10a is locked, excess lengths of the locking limbs 24, 26 may be trimmed proximate to the opposed loops 36, 38.

The pusher tubes 100(1), 100(2) optionally include one or more outriggers 114 extending generally outward from the distal ends 104(1), 104(2) of the pusher tubes 100(1), 100(2), for example, outwardly from the longitudinal axis of the pusher tubes 100(1), 100(2) as generally illustrated in FIG. 21. The outriggers 114 may facilitate pulling the hot sides 108(1), 108(2) of the opposed loops 36, 38 through the pusher tubes 100(1), 100(2). More specifically, the outrigger 114 is configured to provide an increased area against which the forceps or other grasper 112 may contact against.

Figure 22:
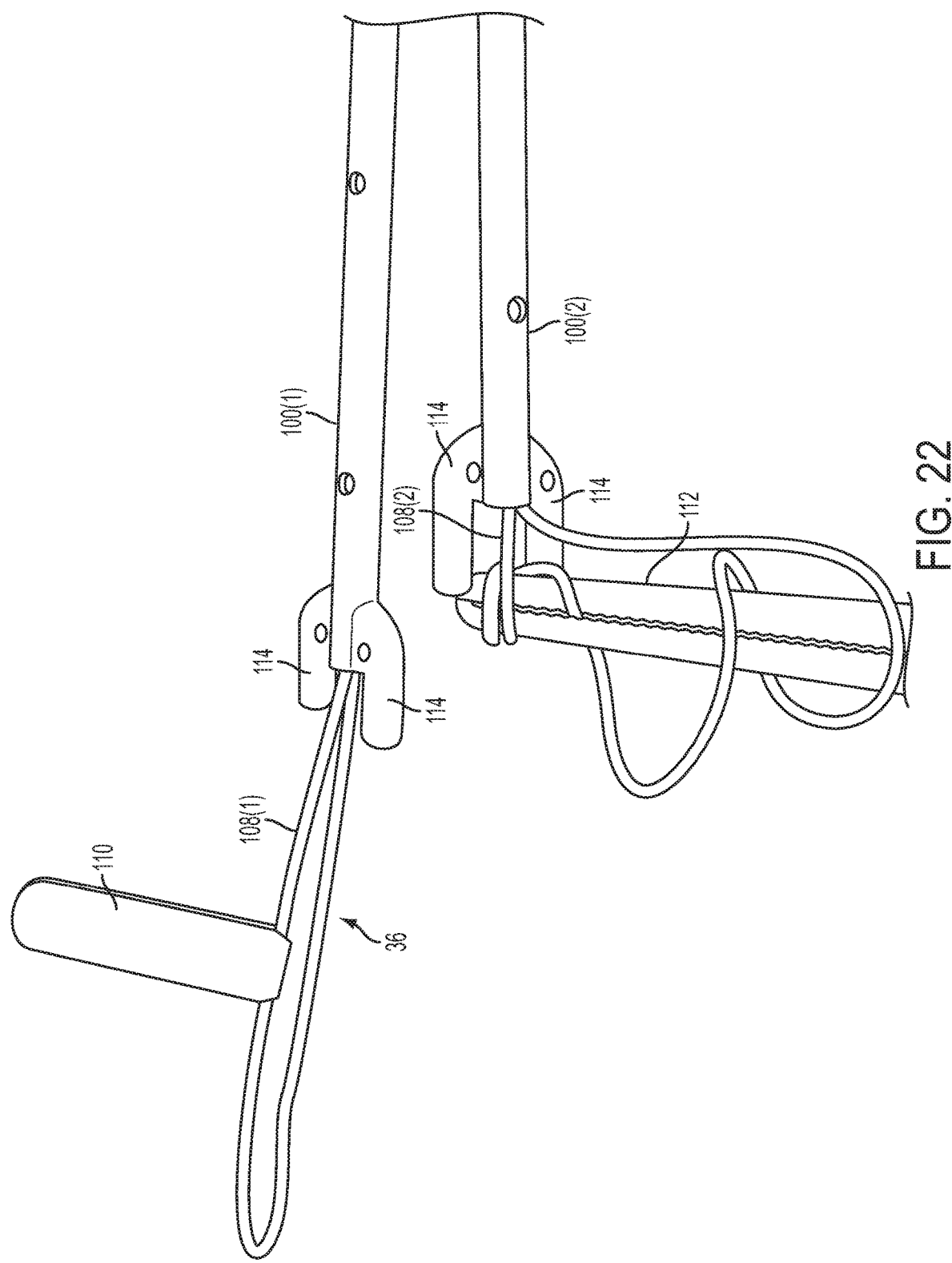
FIG. 22 illustrates another embodiment of the pusher tubes consistent with the present disclosure.
Figure 23:
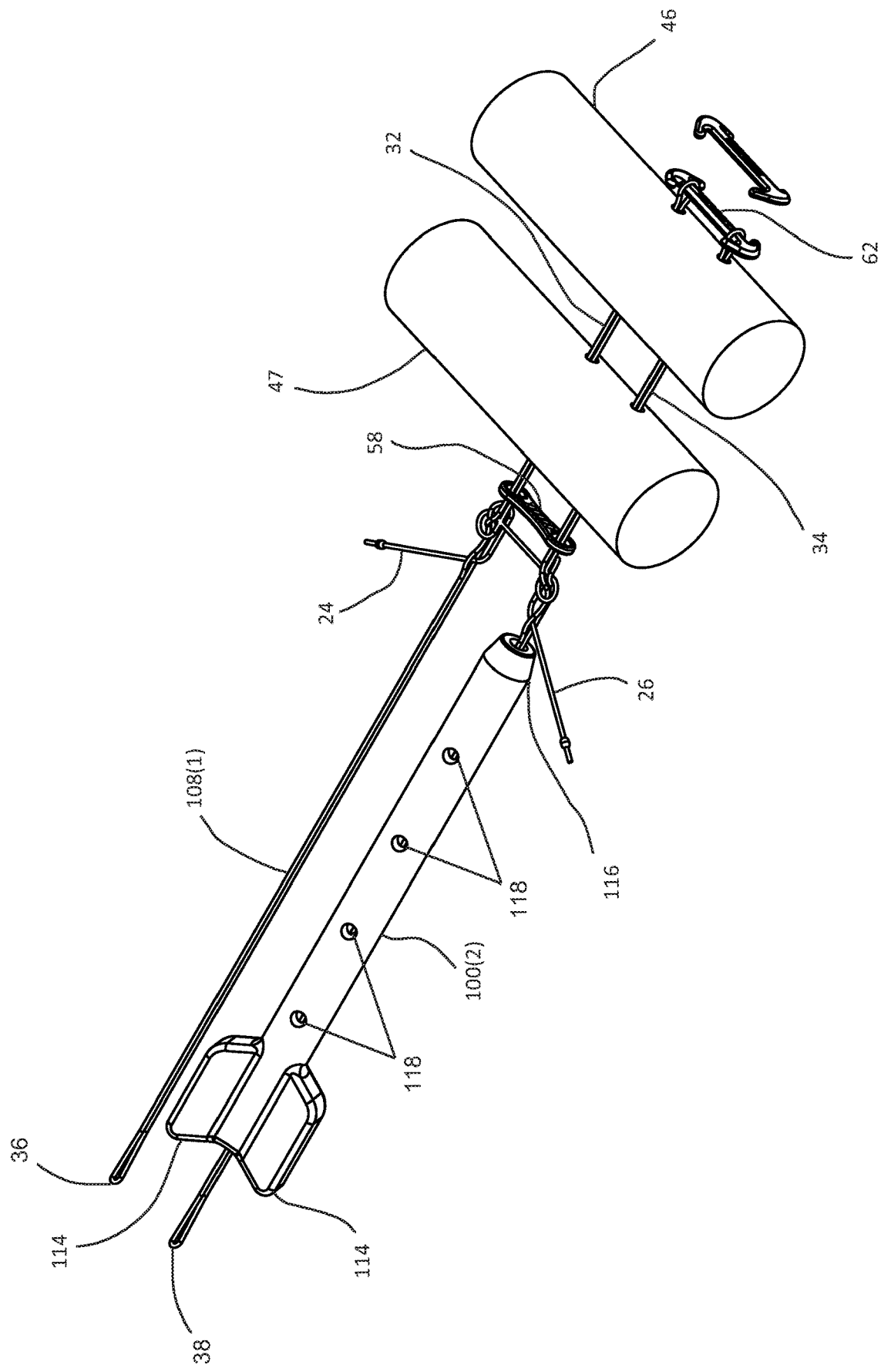
FIG. 23 illustrates a further embodiment of the pusher tubes consistent with the present disclosure.
Figures 24, 25:
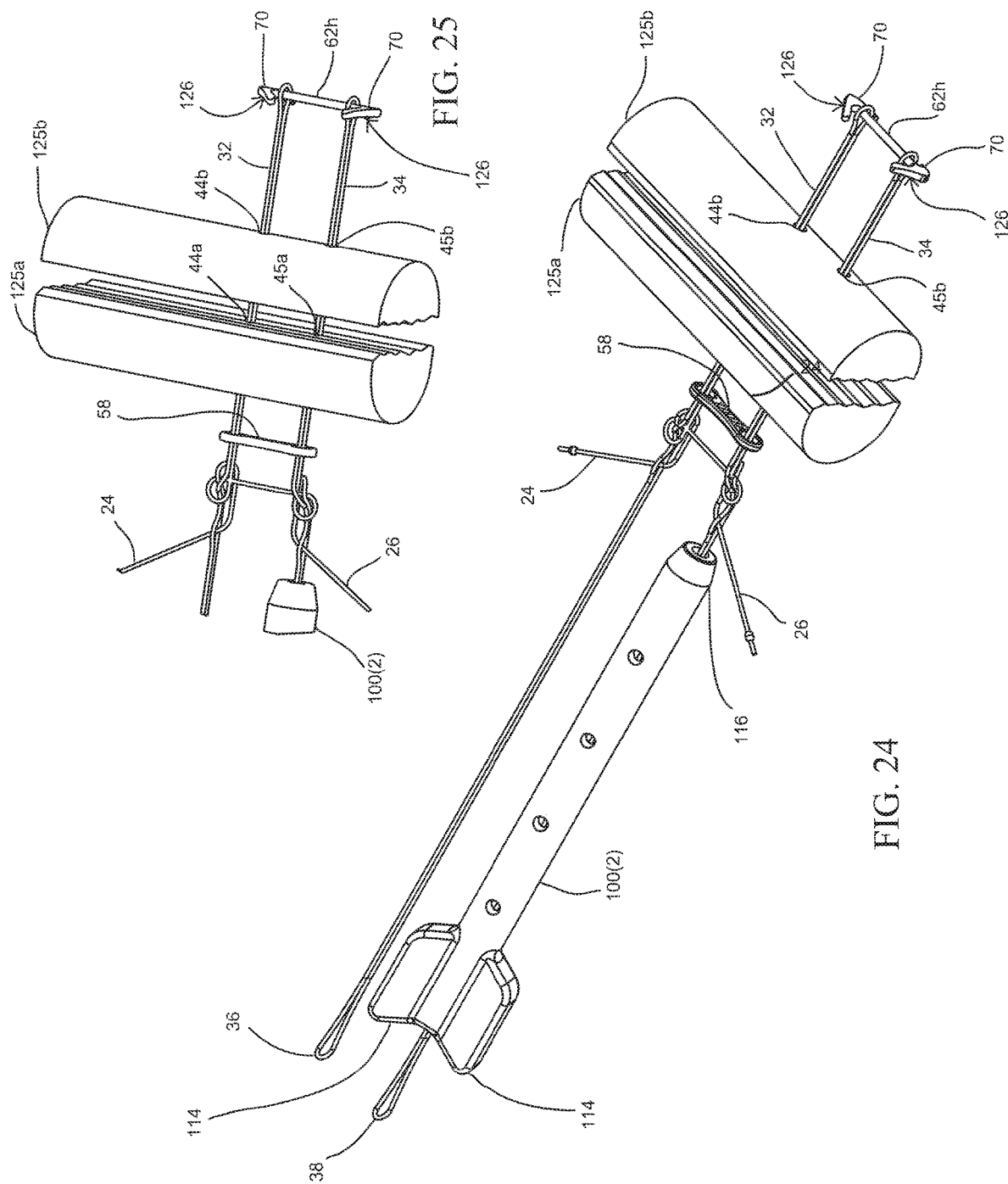
FIGS. 24 and 25 illustrates an embodiment of a suture system in combination with another embodiment of a suture pin for securing two bone fragments.

With reference to FIG. 22, the pusher tubes 100(1), 100(2) may include a plurality of outriggers 114(1)-114(n) extending generally outwardly from the distal ends 104(1), 104(2) of the pusher tubes 100(1), 100(2). For example, the pusher tubes 100(1), 100(2) may include a first and a second outrigger 114(1), 114(n) which extend outward from generally opposite sides of the pusher tubes 100(1), 100(2), e.g., the first and second outriggers 114(1), 114(2) to form a cradle-like structure configured to reduce and/or prevent the forceps/graspers 112 from slipping off the distal ends 104(1), 104(2) of the pusher tubes 100(1), 100(2) as the forceps/graspers 112 are rotated or twisted. For example, the first and second outriggers 114(1), 114(2) may be disposed approximately 180 degrees from each other. It should be appreciated, however, that the first and second outriggers 114(1), 114(2) may be disposed at any other angle relative to each other to form a crook. For example, the first and second outriggers 114(1), 114(2) may be disposed at an angle less than 180 degrees relative to each other, for example, an obtuse angle as generally illustrated in FIG. 23.

Optionally, one or more of the proximal ends 160(1), 106(2) of the pusher tubes 100(1), 100(2) may include a taper 116 to aid in visualization of the tip. Additionally, the pusher tubes 100(1), 100(2) may optionally include one or more apertures 118. The apertures 118 may facilitate sterilization of the pusher tubes 100(1), 100(2) by allowing the sterilization medium to more easily flow through the lumens 101(1), 101(2) of the pusher tubes 100(1), 100(2) and/or may facilitate molding of the pusher tubes 100(1), 100(2) by allowing pins to be aligned through the apertures 118 to aid in aligning a centering pins disposed through the lumens 101(1), 101(2).

The pusher tubes 100(1), 100(2) facilitate the reduction of the suture construct 10a. In particular, the pusher tubes 100(1), 100(2) allow the user to pull the suture 12 (e.g., the hot sides 108(1), 108(2)) from the opposed loops 36, 38 linearly through the first and second loops 20, 22, thereby allowing a user to more easily apply a much greater amount of compressive force through the suture system 1a. Moreover, rotating/twisting the hot sides 108(1), 108(2) using the forceps 112 on the distal ends 104(1), 104(2) of the pusher tubes 100(1), 100(2) creates a mechanical advantage (e.g., a pulley-like effect) which greatly increases the amount of compressive force which may be applied through the suture system 1a.

Figure 26:
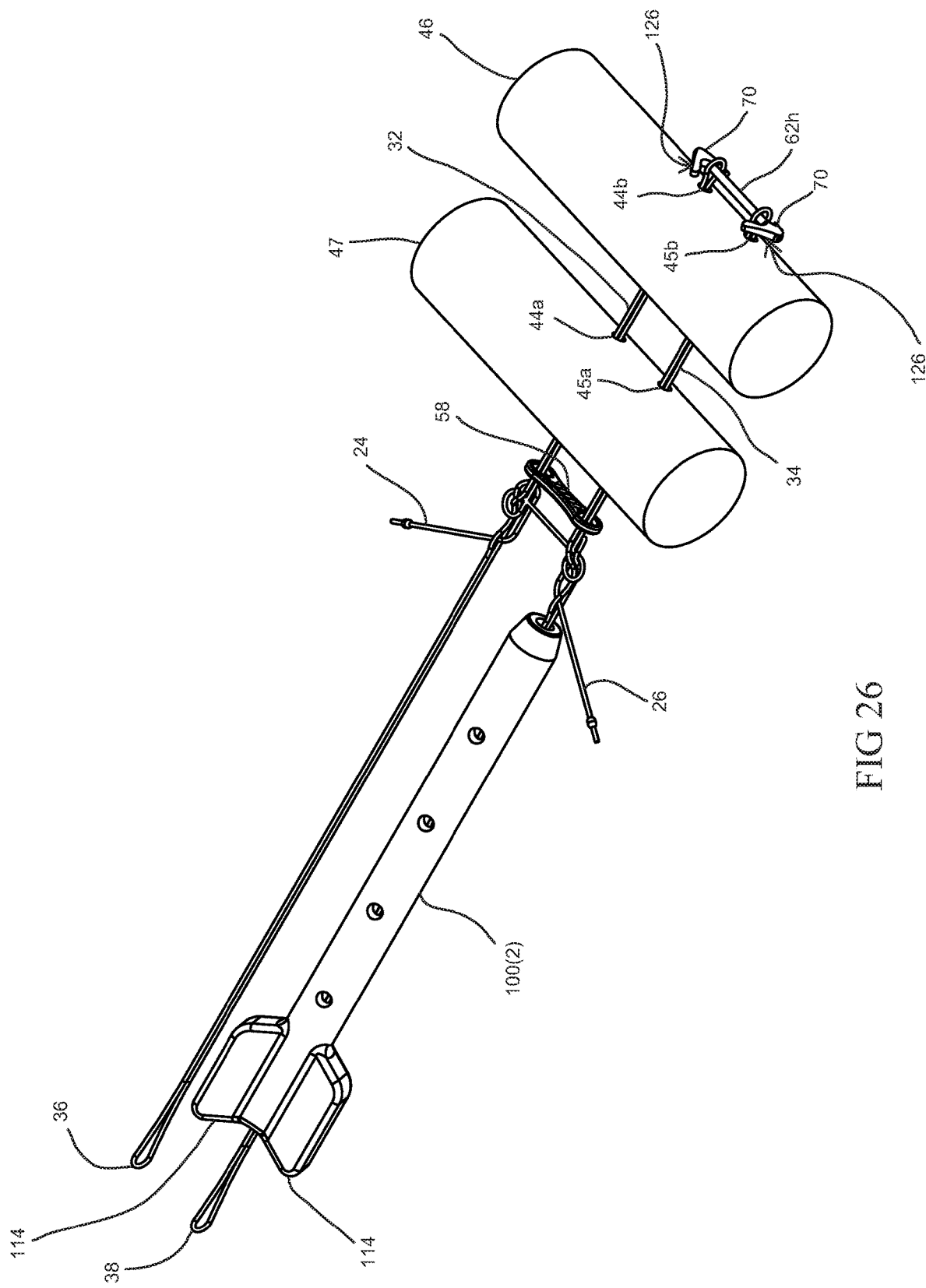
FIG. 26 illustrates an embodiment of a suture system in combination with the suture pin of FIGS. 24 and 25 for securing two bones.

Turning now to FIGS. 24-30, another embodiment of a suture pin 62h is generally illustrated. In particular, FIGS. 24 and 25 generally illustrate one embodiment of a suture construct 10a in combination with the suture pin 62h for securing two bone fragments 125a, 125b. FIG. 26 generally illustrates one embodiment of a suture construct 10a in combination with the suture pin 62h for securing two bones 46, 47. FIGS. 27-30 generally illustrate various views of the suture pin 62h. As will described in more detail herein, the suture pin 62h reduces the amount of friction and/or force required to reduce the suture construct, thereby providing a greater tactile feel to the surgeon, minimizing potential damage to the bones/bone fragments, and/or providing sufficient strength/rigidity to the suture pin to prevent damage/failure of the suture pin while reducing the suture construct.

Figure 31:
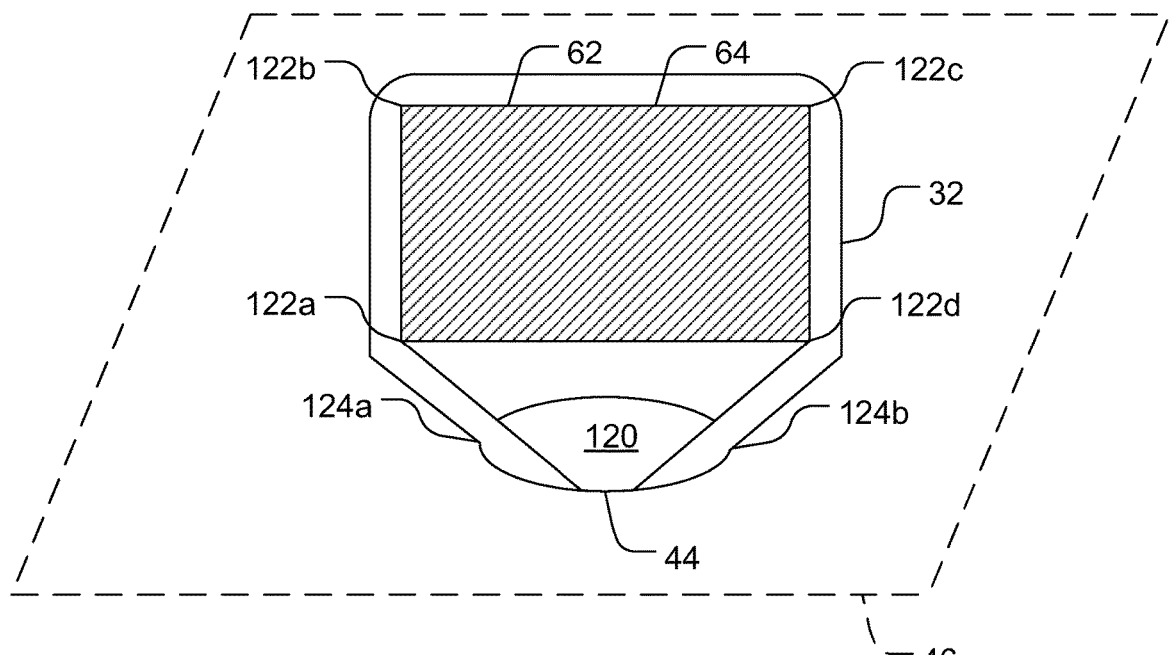
FIG. 31 illustrates a cross-sectional view of one embodiment of a suture pin and a contractible loop extending through an opening in a passageway.

As may be appreciated, the main body of the suture pin should be strong enough to prevent failure when reducing the suture construct. Put another way, if the suture pin is not strong enough, then the forces exerted against the suture pin by the suture construct will excessively bend the suture pin causing an unacceptable amount of deformation of the suture pin which can lead to bone damage or failure of the suture pin. As the cross-sectional thickness of the suture pin is increased, however, the main body of the suture pin begins to close/cover-over the opening in the bone defined by the passageway therethrough. An example of this is illustrated in FIG. 31. In particular, a cross-section of a suture pin 62 and the opening 120 of passageway 44 in the bone 46 is generally illustrated. The suture pin 62 includes a rectangular main body 64 over which the contractible loop 32 slides. Because the cross-sectional thickness of the main body 64 (i.e., the portion of the suture pin which extends across the opening 120) is larger than the diameter of the opening 120 to provide sufficient strength to the suture pin 62, the main body 64 will cover or block the opening 120. As the main body 64 blocks the opening 120, the contractible loop 32 is forced to travel between the main body 64 and the opening 120 and/or the contractible loop 32 is forced to cut a groove into the bone 46 in the area proximate to the opening 120 when the suture construct is reduced. Consequently, the suture pin 62 significantly increases the friction/resistance and reduces the tactile feel when reducing the suture construct.

In addition, the rectangular cross-section of the main body 64 significantly increases the amount of friction when reducing the suture construct. In particular, because the contractible loop 32 is forced to travel between the main body 64 and the opening 120, the contractible loop 32 must slide across the four corners 122a, 122b, 122c 122d of the main body 64 as well as two portion portions 124a, 124b of the perimeter of the opening 120. The four corners 122a, 122b, 122c 122d and portions 124a, 124b generate a very high stress and/or friction concentrations, thereby increasing the overall amount of force necessary to slide the contractible loop 32 when reducing the suture construct.

Referring back to FIGS. 24-30, the suture pin 62h is configured to minimize and/or eliminate the above described issues. In particular, the suture pin 62h includes a main body 64 having a generally circular cross-section extending between a first and a second enlarged portion 70. The main body 64 may include a length which is greater than the spacing of the bridge 18 to compensate for non-parallel passageways 44, 45. For example, for a bridge having a length of 10 mm, the main body 64 may include a length of 17 mm to 20 mm. The diameter of the main body 64 should be selected to prevent an undesirable amount of deformation and/or failure of the suture pin 62h based on the intended use of the suture construct. By way of an example, a suture pin 62h constructed from a titanium alloy used with a suture construct having a #4 suture to treat hallux valgus may include a main body 64 having a diameter of approximately 1 mm (which may be approximately equal to the diameter of the passageway 44). It should be appreciated, thought, that this is just an example, and that the diameter of the main body 64 of the suture pin 62h will depend on the intended application as well as the intended forces exerted by the suture system during reduction.

Figure 32:
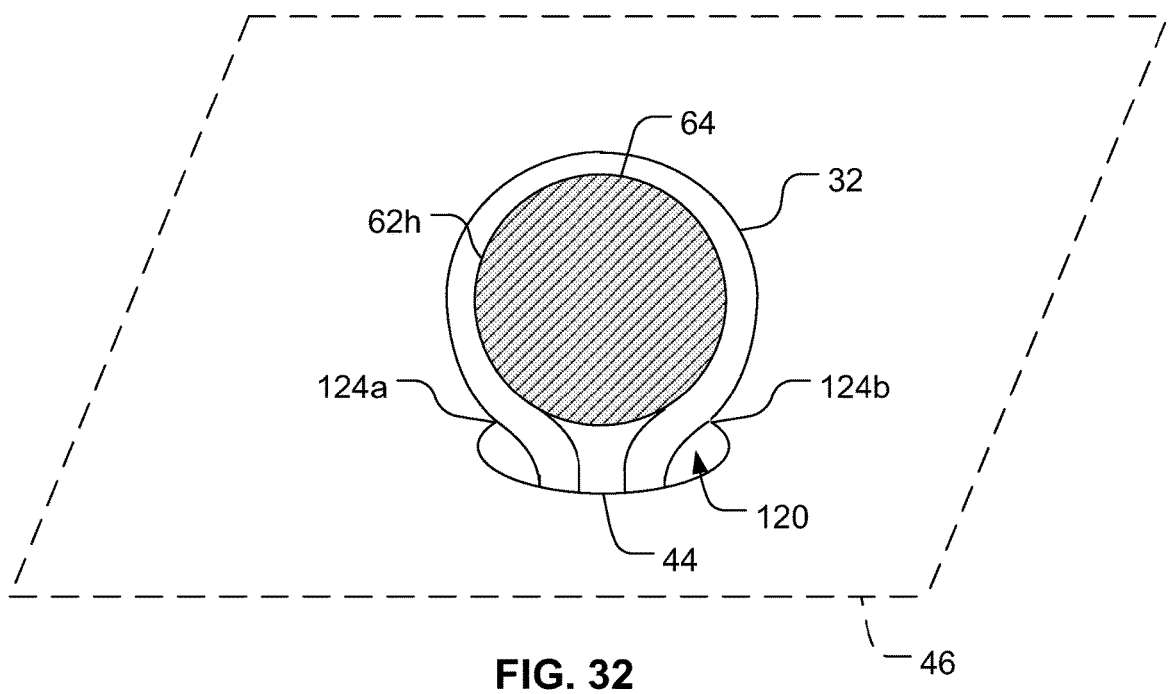
FIG. 32 illustrates a cross-sectional view of the suture pin of FIGS. 24 and 25 and a contractible loop extending through an opening in a passageway.

With reference to FIG. 32, a cross-section of the main body 64 of the suture pin 62h is illustrated along with the contractible loop 32 extending through the opening 120 of the passageway 44. Depending on the diameter of the main body 64, the suture pin 62h may eliminate the friction points (e.g., when the diameter of the main body 64 is less than the diameter of the opening 120 of the passageway 44) or may have only two friction points 104a, 124b which correspond to the locations where the contractible loop 32 passes between the main body 64 and the opening 120 (e.g., when the diameter of the main body 64 is equal to or greater than the diameter of the opening 120 of the passageway 44). The generally circular cross-section of the main body 64 acts as a pulley, thereby allowing the contractible loop 32 to slide smoothly around a portion of the perimeter of the main body 64 (e.g., greater than or equal to 180 degrees around the main body 64) as the contractible loop 32 is reduced. As a result, the suture pin 62h with a main body 64 having a generally circular cross-section reduces the amount of friction and/or force required to reduce the suture construct. Additionally, the reduction in friction points allows the suture pin 62h to provide a greater tactile feel to the surgeon and minimizes potential damage to the bones/bone fragments. Moreover, the overall strength of the suture pin 62h may be increased while preventing/minimizing the suture pin 62h from covering/blocking the opening 120 of the passageway 44.

With reference again to FIGS. 24-30, the enlarged portions 70 of the suture pin 62h may include a bone facing surface 126 having a generally concaved contour. The concaved contour is configured to allow the bone facing surface 126 to generally conform to the bone surface, e.g., to allow the bone facing surface 126 to sit generally congruent with the bone face. The concaved bone facing surface 126 helps distribute the forces exerted by the suture system more evenly across the bone 46 and also helps position the suture pin 62h during assembly/implanting of the suture system within passageway(s) 44, 45.

One or more of the enlarged portions 70 of the suture pin 62h may also feature one or more shoulders 127 extending outwardly beyond the main body 64. For example, the shoulders 127 may form a generally an arrowhead-like shape which extend outward and generally towards the opposite end (though the shoulders 127 may extend outward generally perpendicularly from the main body 64 or outward generally away from the opposite end). As discussed herein, the enlarged portions 70 may aid in keeping the contractible loop(s) 32, 34 disposed on the main body 64 during assembly/implanting of the suture system within passageway(s) 44, 45.

While the main body 64 is described having a generally circular cross-section, it may be appreciated that the main body 64 may also include a generally oval cross-section. Additionally, while the entire main body 64 is illustrated having a generally circular, it may be appreciated that only the portions or regions of the main body 64 over which the contractible loop(s) 28, 30 slide when reducing the suture construct may have a generally circular or oval cross-section. Moreover, while the suture pin 62h is illustrated having a first and a second enlarged portion 70, it may be appreciated that the main body 64 may extend between one or more reduced portions as disclosed herein.

Variations of the suture system and suture construct described herein are considered to be part of this disclosure. For example, while the suture construct the suture construct described above is generally symmetrical about the bridge (e.g., the suture construct is illustrated having first and second knots, first and second loops, first and second contractible loops, and first and second opposed loops separated by the bridge), the bridge section may be eliminated and the suture construct may feature only one half of the remaining construct (i.e., a single reduction construct). More specifically, the suture construct may alternatively include only one knot, one loop, one contractible loop, and one opposed loop. The contractible loop may be passed through a single passageway formed through the first and second bones. A first suture pin may be disposed through a distal end of the contractible loop against the first bone and a second splice pin may be disposed through a proximal end of the contractible loop against the second bone. The suture construct may then be tightened by pulling on the locking limb of the suture using a pusher or pusher tube as generally described herein. Once the desired amount of force is applied by the suture construct, the tension on the suture construct causes the opposed loop to reduce against the locking limb, thereby locking the suture construct and preventing the suture construct from loosening. Once the suture construct is locked, the locking limb may be trimmed proximate to the opposed loop.

One or more of the suture systems consistent with the present disclosure provide numerous advantages. For example, the suture systems may include an all thread (suture) repair device which does not require the surgeon to tie any knots, welds, or the like in order to secure and/or draw the suture system tight. The elimination of knots is significant because many surgeons are uncomfortable tying knots due to the possibility of the knot becoming loose and/or the difficulty associated with tying a knot during a surgical procedure. Additionally, welding increases the possibility of accidental collateral damage to surrounding tissue and may be difficult during a surgical procedure.

Additionally, the suture systems consistent with the present disclosure eliminate the need to pass buttons, pledgets, or the like through passageways formed in the bone. As a result, the passageways formed in the bone may have a smaller diameter and may minimize the potential of causing incidental complications (such as, but not limited to, damaging the bones during drilling and/or cracking the bones after installation).

The suture systems consistent with the present disclosure also provide an "equilibrium" construct. More specifically, the suture systems consistent with the present disclosure distribute the compressive force generated by the suture system evenly across the entire suture system. In contrast, other suture systems utilize two separate and distinct sutures. Consequently, one suture may exert more compressive force than the other suture. This uneven compressive force may place additional stress on the tissue and/or bones, and may lead to the tissue or bones failing.

According to one aspect, the present disclosure features a suture system including a suture construct having a first reduction construct configured to be selectively arranged in an expanded state and a reduced state. The first reduction construct includes a first locking limb, a first contractible loop, and a first opposed loop disposed generally opposite to the first contractible loop, wherein reduction of the first opposed loop contracts the first contractible loop from the expanded state into the reduced state and secures the suture construct in the reduced state. The suture construct may also include a second reduction construct.

According to another aspect, the present disclosure features a suture system including a first and a second reduction construct separated by a bridge. Each of the reduction constructs features a knot defining a loop, a contractible loop and an opposed loop separated by the loop, and a locking limb extending from the loop and the opposed loop. Each of the reduction constructs is configured to be selectively reduced from an expanded state to a reduced state by reducing a length of the contractible loop by urging the locking limb through the loop from the opposed loop, thereby advancing a portion of the contractible loop through the loop and into the opposed loop.

According to yet another aspect, the present disclosure features a suture system including a first and a second reduction construct separated by a bridge. Each of the reduction constructs is configured to be selectively arranged in an expanded state and a reduced state and each includes a locking limb, a contractible loop, and an opposed loop disposed generally opposite to the contractible loop. Reduction of the opposed loop contracts the contractible loop from the expanded state into the reduced state and secures the suture construct in the reduced state.

According to yet a further aspect, the present disclosure features a suture pin including a first and a second enlarged portion and an elongated body portion extending between the first and the second enlarged portion. The elongated body portion has a generally circular cross-section. The first and the second enlarged portion have a cross-section which greater than a cross-section of the elongated body portion.

According to another aspect, the present disclosure features a method for securing two bones together using a suture system. The method includes forming a first and a second passageway, each extending through a first and a second bone; advancing a distal portion of a first and a second contractible loop through a respective one of the first and the second passageways until the distal ends extend beyond the first bone, wherein proximal regions of the first and the second contractible loops are separated by a bridge, the bridge being disposed proximate to the second bone; advancing a suture plate through the distal portion of the first and the second contractible loops extending beyond the first bone; and reducing the first and the second contractible loops disposed within the first and the second passageways by advancing a first and a second locking limb from a first and a second opposed loop and through a first and a second loop, respectively, thereby advancing portions of the first and second contractible loops through the first and the second loops and into the first ands second opposed loops.

According to yet a further aspect, the present disclosure features a method for forming a suture construct. The method includes providing a length of suture; forming a first and a second knot and a first and a second loop, respectively, in the suture, the first and second knots being separated by a bridge; and passing intermediate portions of the suture through the first and the second loops to form a first and a second contractible loop and a first and a second opposed loop, respectively, wherein a first and a second locking limb extends from the first and the second opposed loops through the first and the second loops, respectively.

It should be appreciated that various features of the different embodiments described herein may be combined together.

While the principles of the present disclosure have been described herein, it is to be understood by those skilled in the art that this description is made only by way of example and not as a limitation as to the scope of the invention. The features and aspects described with reference to particular embodiments disclosed herein are susceptible to combination and/or application with various other embodiments described herein. Such combinations and/or applications of such described features and aspects to such other embodiments are contemplated herein. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

Additional disclosure in the format of claims is set forth below:

What is claimed is:

1. A suture system comprising:
   a suture construct including a reduction construct configured to be selectively arranged in an expanded state and a reduced state, said reduction construct comprising:
   a locking limb;
   a contractible loop; and
   an opposed loop disposed generally opposite to said contractible loop, wherein reduction of said opposed loop contracts said contractible loop from said expanded state into said reduced state and secures said suture construct in said reduced state;
   a suture plate coupled to a first end of the suture construct and configured to be placed against a first bone; and
   a suture pin coupled to a second end of the suture construct and configured to be placed against a second bone, such that the suture construct extends between the suture plate and the suture pin;
   wherein the suture construct is configured to secure the first bone with the second bone towards each other via tensioning the locking limb; and
   wherein said contractible loop and said opposed loop are separated by a first loop defined by a first knot.

2. The suture system of claim 1, wherein the suture construct is configured to extend through a passageway between one or both of the first bone and the second bone.

3. The suture system of claim 2, wherein the suture pin comprises a dimension larger than a maximum dimension of the passageway.

4. The suture system of claim 2, wherein the suture plate comprises a dimension larger than a maximum dimension of the passageway.

5. The suture system of claim 1, wherein the suture plate comprises one or more apertures for receiving at least a portion of the suture construct.

6. The suture system of claim 1, wherein a length of said contractible loop is reduced by pulling said locking limb, causing a portion of said suture construct to pass from said first contractible loop and through said first knot, and through said first opposed loop.

7. The suture system of claim 1, wherein a first portion of said opposed loop extends through said first loop from said contractible loop, and wherein a second portion of said opposed loop extends through said first loop and terminates at said locking limb.

8. The suture system of claim 7, wherein a first portion of said contractible loop extends through said first loop from said opposed loop, and wherein a second portion of said contractible loop extends from and terminates at said first knot.

9. The suture system of claim 1, wherein a length of said contractible loop is reduced by pulling said locking limb, causing a portion of said suture to pass from said contractible loop and through said first knot, and through said opposed loop.

10. The suture system of claim 1, wherein said locking limb is configured to be disposed through said opposed loop to lock said suture construct.

11. The suture system of claim 1, wherein the suture plate comprises a generally rectangular cross-section.

12. The suture system of claim 1, wherein the suture construct comprises of one or more sutures.

13. The suture system of claim 12, wherein the one or more sutures comprises woven sutures, non-woven sutures, or both.

14. The suture system of claim 12, wherein the one or more sutures comprises an absorbable material, a non-absorbable material, or both.

* * * * *